United States Patent [19]

Lee et al.

[11] Patent Number: 5,156,670
[45] Date of Patent: Oct. 20, 1992

[54] CYCLIC ALKYLIDENE SUBSTITUTED PYRIDINE HERBICIDES

[75] Inventors: Len F. Lee, St. Charles; Kathleen K. Smith, St. Louis; Karey A. Van Sant, St. Charles, all of Mo.

[73] Assignee: Monsanto Company, St. Louis, Mo.

[21] Appl. No.: 709,463

[22] Filed: Jun. 3, 1991

[51] Int. Cl.$^5$ .................. C07D 405/06; A01N 43/40
[52] U.S. Cl. ........................................ 71/94; 71/90; 71/92; 546/283; 546/284; 546/275; 546/280; 546/281; 546/278
[58] Field of Search ............... 546/283, 284, 275, 280, 546/281, 278; 71/90, 92, 94

[56] References Cited

U.S. PATENT DOCUMENTS 5,019,153  5/1991  Lee et al. ................... 71/94
5,037,469  8/1991  Hegde et al. ............... 71/94

*Primary Examiner*—Jane T. Fan
*Attorney, Agent, or Firm*—Grace L. Bonner; George R. Beck; Howard C. Stanley

[57] ABSTRACT

Fully substituted pyridines having a cyclic alkylidene substituent, useful as herbicides, compositions and methods of use thereof.

21 Claims, No Drawings

CYCLIC ALKYLIDENE SUBSTITUTED PYRIDINE HERBICIDES

This invention relates to a new class of substituted pyridinecarboxylic acid derivatives having a wide range of activity as herbicides.

Pyridine derivatives have, for many years, been investigated for use in biological sciences. For example, 2,6-bis(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic groups wherein the hetero atom is oxygen or sulfur.

In EPO patent 44,262 there are disclosed 2,6-dialkyl-3-phenylcarbamyl-5-pyridinecarboxylates and 5-cyano-compounds useful as herbicides. There is no disclosure of the 2-haloalkyl radicals or any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4-position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in U.S. Pat. No. 4,692,184. These compounds have fluorinated methyl groups at the 2- and 6-positions and carboxylic acid derivative at the 3- and 5-positions.

Other pyridinedicarboxylate compounds including pyrazole amides are disclosed in U.S. Pat. No. 4,698,093. U.S. Pat. No. 4,988,384 discloses pyridines substituted at the 3- and/or 5-position(s) with a heterocyclic moiety. U.S. Pat. No. 4,066,438 and 4,180,395 disclose various herbicidal polyhalo substituted pyridyloxy compounds.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

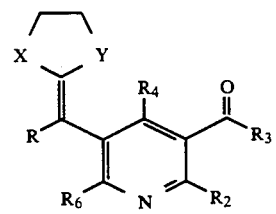

R is hydrogen, cyano, halo, or lower alkoxycarbonyl;

$R_2$ and $R_6$ are independently lower alkyl, chloromethyl, fluoromethyl, chlorofluoromethyl, lower alkoxy, or lower dialkoxyalkyl, provided that one of $R_2$ and $R_6$ must be a fluoromethyl or chloromethyl;

$R_3$ is hydroxy, lower alkoxy, lower alkylthio, haloalkoxy, lower alkenyloxy, lower alkynyloxy, (di)alkylamino, or phenylamino;

$R_4$ is $C_1$-$C_4$ straight or branched chain alkyl, $C_3$-$C_4$ cycloalkyl, cycloalkylalkyl, haloalkyl, lower alkoxyalkyl, lower alkylthioalkyl, or dialkylaminoalkyl;

X and Y are independently O, S, $CH_2$, CHR', CR'R", or NHR''';

R' and R" are independently lower alkyl, halo, cyano, hydroxy, lower alkoxy, or lower alkylthio; and R''' is hydrogen or lower alkyl.

The term "lower" used herein for lower alkyl, lower alkoxy or like group means a group containing 1-7 carbon atoms in straight or branched chain form. Specifically, the lower alkyl group may be methyl, ethyl, propyl, isopropyl, butyl, isobutyl, pentyl, isopentyl or hexyl; and the lower alkoxy group may be methoxy, ethyoxy, propoxy, isopropoxy; the lower alkylthio group may be methylthio, ethylthio, propylthio, isopropylthio, butylthio or pentylthio. The lower alkenyl or lower alkynyl group have 3 to 7 carbon atoms and may be vinyl, allyl, isopropenyl, 2-butenyl, 1,3-butadienyl, 2-pentenyl, 1,4-pentadienyl, 1,6-heptadienyl, 1-hexenyl, ethynyl, 2-propynyl, etc.

The term "halo" or cognates thereof include chlorine, bromine, fluorine and iodine.

Examples of "cycloaklyl" as used herein include cyclopropyl, cyclobutyl, cyclopentyl, and cyclohexyl.

Examples of "lower haloalkyl" as used herein include chloromethyl, bromomethyl, dichloromethyl, dibromomethyl, trifluoromethyl and the like.

Examples of "lower haloalkoxy" as used herein include chloroethyoxy, bromoethoxy, dichloroethoxy, dibromoethoxy, trifluoroethoxy, and the like.

Examples of "lower alkoxyalkyl" as used herein include methoxymethyl, ethoxymethyl, propoxymethyl, butoxymethyl and the like.

Examples of "dialkylaminoalkyl" as used herein include N,N-dimethylaminomethyl and N,N-diethylaminomethyl.

Examples of "(di)alkylamino" as used herein include N,N-dimethylamino, N,N-diethylamino, N-methylamino, N-ethylamino, N-propylamino, and N-butylamino.

Examples of "lower alkylthioalkyl" as used herein include methylthiomethyl, ethylthiomethyl, methylthioethyl, ethylthioethyl and the like.

Examples of "lower alkoxycarbonyl" as used herein include methoxycarbonyl, ethoxycarbonyl, propoxycarbonyl, isopropoxycarbonyl and the like.

The term "cycloalkylalkyl" means a $C_1-C_2$ alkyl groups substituted with a $C_3-C_6$ cycloalkyl group, such as cyclopropylmethyl, cyclopropylethyl, cyclobutylmethyl, cyclopentylethyl, and so forth.

The terms "fluoromethyl", "chloromethyl", and "chlorofluoromethyl" means methyl radicals wherein one or more of the three hydrogen atoms have been replaced by a fluorine atom, a chlorine atom, or a flourine atom and a chlorine atom, respectively.

The preferred compounds of the present invention are those in which one of $R_2$ and $R_6$ is a difluoromethyl and the other is a trifluoromethyl group and $R_3$ is an alkoxy, more preferably methoxy. More preferred are these compounds in which X is $CH_2$ and Y is O. Of these preferred compounds, the compound wherein R is cyano and $R_4$ is 2-methylpropyl has a highly desirable physical property, i.e., a very low Henry's constant, 0.036 mPa L/mol. This property indicates very low soil mobility, which is desired for season-long activity.

DETAILED DESCRIPTION OF THE INVENTION

The novel herbicidal compounds of this invention are readily prepared from known monoesters of substituted 3,5-pyridinedicarboxylic acids. Many of the starting materials are disclosed in U.S. Pat. Nos. 4,692,184 (Lee 9/87) and 4,826,532 (Sing et al. 5/89), the full texts of both of which are incorporated herein by reference.

Intermediate compounds are prepared by converting the appropriate monoacid to the acid chloride, thus producing chlorocarbonylpyridinecarboxylates. The acid chloride groups may be converted to hydroxymethyl groups by known methods from which various compounds may be made. For example, the hydroxymethyl may be converted to a formyl by known methods. Alternatively, it may be converted to a chloromethyl which in turn may be converted to a cyanomethyl group by reaction with sodium cyanide. These intermediates are the basis for the compounds of the present invention.

From the cyanomethylpyridinecarboxylate intermediates, one may prepare the compounds of the present invention wherein R is cyano. This is accomplished by reaction with the appropriate haloalkylcarbonyl halide, for example, 4-bromobutyryl chloride, 4-chlorobutyryl chloride, 2-bromoethylchloroformate, 1-methyl-4-chlorobutyryl chloride, or 2,2-dimethyl-4-bromobutyryl chloride, under usual conditions for cyclization, for example, under a phase transfer catalyst such as benzyltriethylammonium chloride.

The cyclic group thus produced may be further derivatized. For example, one or two chloro groups may be added by metallization. The monochloro derivative may be further reacted with nucleophiles to produce various compounds of the present invention. Such nucleophiles may be, for example, $SCH_3$, SCN, or OH.

The compounds of the present invention wherein R is a hydrogen may be prepared from the formyl intermediates described above. Reaction with the appropriate cyclic phosphorane derivative under Wittig reaction conditions or with the appropriate cyclic triphenyl phosphine oxide will produce the desired compounds.

Cyclopentylidenemethyl derivatives are prepared by reaction of the appropriate formyl intermediate with cyclopentyl magnesium chloride, followed by dehydration. The cyclopentyl ring may be further substituted by various groups using known reactions. Unexpectedly, reaction with bromine will add a bromine to the ring instead of reacting with the double bond.

After the desired ring has been added to the pyridinecarboxylate the other substituents on the ring may be transformed to produce other compounds of the present invention. For example, to obtain compounds wherein $R_3$ is other than an alkoxy group, the ester is converted to the acid ($R_3$ to OH) by treatment with an alkalki metal hydroxide, for example, potassium hydroxide. The acid is then converted to the acid chloride using conventional methods such as with thionyl chloride. The acid chloride is then conveniently converted to other desired derivatives by methods known to those of ordinary skill in the art.

Another example of later conversion of other substituents is for $R_2$ and $R_6$. These substituents may be obtained by preparing the appropriate 3,5-pyridinedicarboxylic acid as described in U.S. Pat. Nos. 4,692,184 and 4,826,532 mentioned above. Alternatively, compounds of the present invention wherein $R_2$ or $R_6$ is difluoromethyl may be converted to the dichloromethyl derivative by treatment with aluminum chloride. The 2- or 6-dichloromethyl group may be hydrogenated under usual conditions to prepare the 2- or 6-methyl derivatives or it may be selectively hydrogenated by using only one equivalent of base to produce the monochloromethyl group. Alternatively, the dichloromethyl group may be treated with an alkoxide to produce a dialkoxyalkyl, for example, dimethoxymethyl.

The $R_4$ group may also be transformed after addition of the cyclic alkylidene substituent. For example, an alkylthioalkyl group may be converted to a haloalkyl, which in turn may be converted to a dialkylaminoalkyl group, using conventional methods.

SYNTHESIS EXAMPLES

The following Examples a–f demonstrate preparation of the staring materials for the compounds of the present invention.

EXAMPLE A (1) 2-(Difluoromethyl)-4-(2-methylpropyl)-6-(trifluoromethyl)-3,5-pyridinedicarbonyl dichloride. 2-(Difluoromethyl)-4-(2-methylpropyl)-6-(trifluoromethyl)-3,5-pyridinedicarboxylic acid, prepared as in Example 43 of U.S. Pat. No. 4,692,184, (5,375.2 g, 15.8 mol) in 8 L of toluene and thionyl chloride (5 kg, 42.0 mol) were placed in a 22 L flask with stirring. To this was added 90 mL N,N-dimethylformamide (DMF). The mixture was heated to reflux for five hours and allowed to cool overnight. The solvent was removed on a rotovap with final stripping at 70° C. and 0.3 mmHg. The product was diluted 2:1 with hexane and eluted sequentially through two 20 cm × 12 cm i.d. silica gel columns using hexane as the eluent. Solvent was stripped off on the rotovap at 60° C. and 0.5 mmHg. Obtained was 5454.49 g of the desired product having 99.0% purity by GC, a yield of 91.5%.

(2) 5-(Chlorocarbonyl)-2-(difluoromethyl)-4-(2-methylpropyl)-6-(trifluoromethyl)-3-pyridinecarboxylic acid, methyl ester. A 22 L flask was charged with 8 L tetrahydrofuran (THF), 1 L methanol, and 5454.5 g (14.5 mol) of the diacid chloride of step (1). The solution was stirred for 48 hours. Solvent was removed on the rotovap at 60° C. and 0.3 mmHg. Obtained was 5425.2 g of the desired product having a 98.4% GC purity, a 100% yield.

(3) 2-(Difluoromethyl)-b 5-hydroxymethyl-4-(2-methylpropyl)-b 6-(trifluoromethyl)-3-pyridinecarboxylic acid, methyl ester. Sodium borohydride (24.21 g, 0.64 mol) and 700 mL diglyme were placed in a 3 L flask and cooled to 10° C. The product of step (2), 118.5 g, (0.32 mol), dissolved in 100 ml diglyme was added dropwise. The mixture was allowed to stir at room temperature for 2 hours and cooled to 5° C. Under a $N_2$ sweep, conc. HCl (150 mL) was added dropwise. Aqueous diglyme HCl was removed on the rotary evaporator at 75° C. and 0.1 torr. Resultant crude product was dissolved in 300 ml dichloromethane and washed three times with 100 mL water. The organic layer was separated, dried over magnesium sulfate, filtered and the solvent evaporated on a rotovap. The resulting oil was kugelrohr distilled at 110° C. at 0.04 torr. Final purification by HPLC and rotovap yield 93.65 g of the desired product, an 85.8% yield. m.p. 65°–67° C.

(4) 2-(Difluoromethyl)-5-formyl-4-(2-methylpropyl)-6-(trifluoromethyl)-b 3-pyridinecarboxylic acid, methyl ester. To a 2 L round-bottom flask were added pyridinium chlorochromate (55.18 g, 0.256 mol), oven dried celite (50 g), and 400 mL dichloromethane. To this solution was added the pyridine alcohol produced in step (3) (70.0 g, 0.295 mole), dissolved in 400 mL dichloromethane. The mixture was stirred overnight at room temperature and then filtered through celite. The organics were extracted two times with 0.5 M HCl, dried and removed to yield a dark liquid. This liquid was dissolved in ether, some celite was added, and again filtered, dried and evaporated to yield 64.2 g of the desired product which was purified by kugelrohr distillation to yield 57.8 g of the desired product as a yellow liquid, an 83% yield. b.p. 116° C.

EXAMPLE B (1) 4-(Cyclopropylmethyl)-b 2-(difluoromethyl)-6-(trifluoromethyl)-3,5-pyridinedicarboxylic acid. A 22 L flask was charged with 3884.4 g (9.83 mol) of 4-(cyclopropylmethyl)-2-(difluoromethyl)-b 6-(trifluoromethyl)-3,5-pyridinedicarboxylic acid diethyl ester, prepared as in Example 166 of U.S. Pat. No. 4,692,184, and 3 L ethanol. To this solution 3.5 kg (53.0 mol) 85% potassium hydroxide dissolved in 8 L water was added with stirring. The mixture was then refluxed with stirring overnight. It was cooled and extracted twice with 3 L methylene chloride. The aqueous layer was acidified with 12 N HCl to pH 5–6 and extracted three times with 3 L methylene chlordie. The organic layers were each back-extracted with water and discarded. The combined aqueous layers were acidified to pH<1 with 12 N HCl and extracted twice with 3 L methylene chloride. The combined organic layers were dried over magnesium sulfate and filtered. The solvent was removed under vacuum with drying at 100° C. The yield was 2952.3g of the desired diacid, a yield of 88.6%.

(2) 4-(Cyclopropylmethyl)-b 2-(difluoromethyl)-6-(trifluoromethyl)-3,5-pyridinedicarbonyl dichloride. A 22 L flask was charged with 1999.3 g (5.89 mol) of the diacid of step (1), 5 L toluene, 2 kg (16.8 mol) thionyl chloride and 30 mL DMF. The mixture was refluxed for 2 hours. The solvent and excess thionyl chloride were removed by evaporation. The crude product was diluted with 2 L hexane and eluted through a 15 cm × 12 cm i.d. column of silica gel using hexane as the eluent. After removal of solvent at 60° C. and 10 mmHg, 2048.3 g of the desired product was obtained having 97% GC purity, a yield of 92.4%.

(3) 5-Chlorocarbonyl-4-(cyclopropylmethyl)-b 2-(difluoromethyl)-6-(trifluoromethyl)-3-pyridinecarboxylic acid, methyl ester. A 5 L flask was charged with 994.6 g (2.64 mol) of the diacid chloride of step (2), 3 L THF, and 1 L methanol. After stirring overnight, the solvent was removed by evaporation at 50° C. and 1 mmHg. The desired product, 1012.5 g, was obtained at 94.8% GC purity.

(4) 4-(Cyclopropylmethyl)-2-(difluoromethyl)-5-hydroxymethyl-6-(trifluoromethyl)-3-pyridinecarboxylic acid, methyl ester. The monoacid chloride (1515 g, 4.08 mol), prepared as in step (3), dissolved in 3 L THF, was added slowly to a solution of sodium borohydride (302.6 g, 8.0 mol) in 4 L THF at 0° C. Cooling was maintained at a maximum temperature of 10° C. After the addition was complete the mixture was stirred and allowed to come to room temperature for 2.5 hours. Four liters of 5% HCl were slowly added with cooling. Six L ether were added, and the layers were separated. The organic layer was extracted twice with 4 L (5 M) HCl, dried over magnesium sulfate, filtered and evaporated to yield 1410 g crude product, 92% purity. A portion was purified by chromatography (20/2/1 hexane/EtOAc/methanol) to yield 475 g of the desired product as a light yellow solid. m.p. 62.5°–64° C.

(5) 4-(Cyclopropylmethyl)-2-(difluoromethyl)-5-formyl-6-(trifluoromethyl)-3-pyridinecarboxylic acid, methyl ester. Crude product of step (4), (750 g, 92% pure (2.21 mol)), dissolved in 2 L dichloromethane was added dropwise to a solution of pyridinium chlorochromate (595.7 g, 2.76 mol) and 100 g oven-dried celite in 7 L dichloromethane at room temperature. After stirring overnight, the mixture was filtered through celite and the solvent removed to yield 856 g crude product, which was purified by chromatography and distillation (b.p. 120°–125° C.; 0.2 torr) to yield 635 g of the desired aldehyde as a yellow liquid.

EXAMPLE C (1) 4-(Cyclopropylmethyl)-2-(difluoromethyl)-5-(hydroxymethyl)-6-(trifluoromethyl)-3-pyridinecarboxylic acid, methyl ester. To a 60° C. solution of 0.22 mol of the acid chloride of step 3 of Example b, in 300 mL 1,2-dimethoxyethane (DME) was added 0.65 mol sodium borohydride over two hours. The reaction mixture was stirred at 60° C. for an additional hour and poured into 1 L of ice water causing vigorous gas evolution. Concentrated hydrochloric acid was added slowly to quench excess sodium borohydride. After gas evolution subsided the reaction mixture was extracted with methylene chloride (2×500 mL), dried over magnesium sulfate and concentrated. The residue was kugelrohr distilled at 1 torr to give the desired product.

(2) 5-(Chloromethyl)-4-(cyclopropylmethyl)-2-(difluoromethyl)-6-(trifluoromethyl)-3-pyridinecarboxylic acid, methyl ester. A mixture of 0.03 mol of the compound of step 1, 0.55 mol thionyl chloride and 0.042 mol pyridine was held at reflux for 20 h and concentrated in vacuo. The residue was stirred with 100 mL ether and 100 mL water. The ether layer was washed with brine, dried over magnesium sulfate and concentrated in vacuo. The residue was kugelrohr distilled at 1 torr to give the desired product as a yellow oil.

(3) 5-(Cyanomethyl)-4-(cyclopropylmethyl)-2-(difluoromethyl)-6-(trifluoromethyl)-3-pyridinecarboxylic acid, methyl ester. A mixture of 0.02 mol the compound of step 2, 0.06 mol sodium cyanide, and 25 mL DMF was stirred for 2 h and diluted with 100 mL ether. The ether solution was washed successively with water, brine, and saturated sodium bicarbonate, dried over magnesium sulfate and concentrated in vacuo. The residue was kugelrohr distilled at 1 torr to give the desired product. m.p. 56°–57° C.

EXAMPLE D (1) 5-(Chloromethyl)-2-(difluoromethyl)-4-(2-methylpropyl)-6-(trifluoromethyl)-3-pyridinecarboxylic acid, methyl ester. A mixture of 0.03 mol of the compound of step 3 of Example a, 0.55 mol thionyl chloride and 0.042 mol pyridine was held at reflux for 20 h and concentrated in vacuo. The residue was stirred with 100 mL ether and 100 mL water. The ether layer was washed with brine, dried over magnesium sulfate and concentrated in vacuo. The residue was kugelrohr distilled at 1 torr to give the desired product. $n_D^{25}$ 1.4652.

(2) 5-(Cyanomethyl)2-(difluoromethyl)-4-(2methylpropyl)-6-(trifluoromethyl)-3-pyridinecarboxylic acid, methyl ester. A mixture of 0.02 mol compound of step 1, 0.06 mol sodium cyanide, and 25 mL DMF was stirred for 2 h and diluted with 100 mL ether. The ether solution was washed successively with water, brine, and saturated sodium bicarbonate, dried over magnesium sulfate and concentrated in vacuo. The residue was kugelrohr distilled at 1 torr to give the desired product. m.p. 68°–70° C.

EXAMPLE E (1) 5-Chlorocarbonyl-2-(difluoromethyl)-4-methyl-6-(trifluoromethyl)-3-pyridinecarboxylic acid, methyl ester. A solution of 45.96 g (0.14 mol) of the 3,5-pyridinedicarboxylic acid dichloride of Example 55 in U.S. Pat. No. 4,826,532, in 100 mL methanol was stirred for 1.5 hours and evaporated in vacuo, yielding 45.3 g of crude product, a colorless oil.

(2) 2-(Difluoromethyl)-5-hydroxymethyl-4-methyl-6-(trifluoromethyl)-3pyridinecarboxylic acid, methyl ester. To a solution of 29.55 g (0.09 mol) of the 3-pyridinecarboxylic acid methyl ester of step (1) in 80 mL diglyme was added 10.00 g (0.26 mol) sodium borohydride. The mixture was stirred for 2 hours and partitioned between diethyl ether and dilute hydrochloric acid. The organic layer was washed three times with water and once with brine, dried with magnesium sulfate, filtered, and the filtrate evaporated in vacuo. The residue was kugelrohr distilled, yielding 24. 2 g of the desired product as a yellow oil, an 88% yield.

(3) 5-(Chloromethyl)-2-(difluoromethyl)-4-methyl-6-(trifluoromethyl)-3-pyridinecarboxylic, acid, methyl ester. To a solution of 24.2 g (0.08 mol) of the 5-hydroxymethylpyridine of step (2) in 23.5 g (.020 mol) thionyl chloride was added 1 ml of pyridine. The mixture was stirred for 30 minutes. Excess thionyl chloride was evaporated in vacuo, and the residue was partitioned between diethyl ether and water. The organic layer was washed twice with 10% sodium hydroxide and once with brine, dried with magnesium sulfate, filtered through silica gel, and the filtrate evaporated in vacuo, yielding 26.3 g of crude product, an orange oil.

(4) 5-(Chloromethyl)-2-(difluoromethyl)-4-methyl-6-(trifluoromethyl)-3-pyridinecarboxylic, acid, methyl ester. To a solution of 25.7 g (0.08 mol) of the 5-chloromethylpyridine of step (3) in 150 mL DMF was added 4.50 g (0.09 mol) finely ground sodium cyanide. The mixture was stirred for 30 minutes and partitioned between diethyl ether and water. The aqueous layer was extracted with additional ether, and the combined ether layers were washed with water and then with brine, dried with magnesium sulfate, treated wit decolorizing carbon, filtered through silica gel, and the filtrate evaporated in vacuo. The residue was chromatographed (HPLC, 15% ethyl acetate/hexane), yielding 7.00 g of the desired product as a yellow oil, a 28% yield.

EXAMPLE F (1) 5-(Hydroxymethyl)-2-methoxy-4-(2-methylpropyl)-6-(trifluoromethyl)-3-pyridinecarboxylic acid, methyl ester. To a 60° C. solution of 0.22 mol methyl 5-(chlorocarbonyl)-2-methoxy-4-(2-methylpropyl)-6-(trifluoromethyl)-3-pyridinecarboxylate, prepared as described in pending U.S. application Ser. No. 07/660480, filed Feb. 25, 1991, in 300 mL DME was added 0.65 mol sodium borohydride over two hours. The reaction mixture was stirred at 60° C. for an additional hour and poured into 1 L of ice water causing vigorous gas evolution. Concentrated hydrochloric acid was added slowly to quench excess sodium borohydride. After gas evolution subsided the reaction mixture was extracted with methylene chloride (2×500 mL), dried over magnesium sulfate and concentrated. The residue was kugelrohr distilled at 1 torr to give the desired product.

(2) 5-(Chloromethyl)-2-methoxy-4-(2-methylpropyl)-6-( trifluoromethyl)-3-pyridinecarboxylic acid, methyl ester. A mixture of 0.03 mol of the compound of step 1, 0.55 mol thionyl chloride and 0.042 mol pyridine was held at reflux for 20 h and concentrated in vacuo. The residue was stirred with 100 mL ether and 100 mL water. The ether layer was washed with brine, dried over magnesium sulfate and concentrated in vacuo. The residue was kugelrohr distilled at 1 torr to give the desired product. $n_D^{25}$ 1.4762.

The following Examples 1–40 provide methods for making the compounds of the present invention.

EXAMPLE 1

5-[Cyano(dihydro-2(3H)-furanylidene)methyl]-4-(cyclopropylmethyl) -2-(difluoromethyl)-6-(trifluoromethyl)-3-pyridinecarboxylic acid, methyl ester. 5(Cyanomethyl)-4-(cyclopropylmethyl)-2-( difluoromethyl)-6-(trifluoromethyl)-3-pyridinecarboxylic acid, methyl ester, prepared as in Example c, (3.0 g, 8.6 mmol) was reacted with 4.0 g (21.6 mmol) 4-bromobutyryl chloride in 160 mL dichloromethane and 82 mL 50% NaOH to which was added 0.3 g benezyltriethylammonium chloride. The solution was poured into 175 mL of ice water and extracted with ethyl ether. The organic layer was washed with water and brine and dried over magnesium sulfate. Purification by HPLC (30% EtOAc/hexane) yielded 2.1 g of the desired product as a light yellow oil, a 59% yield. $n_D^{25}$ 1.5028.

EXAMPLE 2

5-[Cyano(dihydro-2(3H)-furanylidene)methyl]-4-( 2-methylpropyl)-2-(difluoromethyl)6-(trifluoromethyl)-3-pyridinecarboxylic acid, methyl ester. To a solution of 5.0 g (14.3 mmol) of 5-(cyanomethyl)4-(2-methylpropyl)-2-( difluoromethyl)-6-(trifluoromethyl)-3-pyridinecarboxylic acid, methyl ester, prepared as in Example d, above, 6.62 g (35.7 mmol) of 4-bromobutyryl chloride and 0.37 g of benzyltriethylammonium chloride in 160 mL dichloromethane was added 82 mL 50% NaOH. The solution turned red and was stirred for 15 min. Stirring was interrupted due to viscosity of solution; 0.5 mL additional 4-bromobutyryl chloride was added to enable stirring. The solution was poured into 175 mL of ice water and extracted with ethyl ether. The organic layer was washed with water, brine, and dried over magnesium sulfate. The solution was filtered through silica gel to give 5.8 g of the crude product as a dark red oil. Purification by chromatography using 30% ethyl acetate in hexanes yielded 1.4 g of the desired product as an oil, a 24% yield. $n_D^{25}$ 1.4882.

EXAMPLE 3

5-(Cyano-1,3-dioxolan-2-ylidenemethyl)-2-(difluoromethyl)-4-(2-methylpropyl)-6-(trifluoromethyl)-3-pyridinecarboxylic acid, methyl ester. To a solution of 5.0 g (14.3 mmol) of 5-(cyanomethyl)-4-(2-methylpropyl)-2-(difluoromethyl)-6-(trifluoromethyl)-3-pyridinecarboxylic acid, methyl ester, prepared as in Example d, above, 8.02 g 2-bromoethyl chloroformate, and 0.3 g benzyltriethylammonium chloride in 125 mL dichloromethane was added 82 mL 50% NaOH. The solution was stirred at room temperature for one hour. The mixture was then poured into ice water and extracted twice with ethyl ether. The organic layer was washed with brine, dried over magnesium sulfate, filtered through silica gel, and concentrated to give 3.2 g of crude dark yellow oil. Chromatography using 50% ethyl acetate in hexanes yielded 2.0 g of the desired product as a light yellow oil, a 56% yield, which crystallized upon standing. m.p. 121°-122° C.

EXAMPLE 4

5-[Cyano(dihydro-3-methyl-2(3H)-furanylidene)methyl]-2-(difluoromethyl)-4-(2-methylpropyl)-6-(trifluoromethyl)-3-pyridinecarboxylic acid, methyl ester. To a solution of 5.0 g (14.3 mmol) of 5-(cyanomethyl)-4-(2-methylpropyl-2-(difluoromethyl)-6-(trifluoromethyl)-3-pyridinecarboxylic acid, methyl ester, prepared as in Example d, above, 5.0 g (34.9 mmol) 1-methyl-4-chlorobutyryl chloride, 0.37 g benzyltriethylammonium chloride, and 150 mL dichloromethane was added 82 mL 50% NaOH. The solution was stirred at room temperature for 2 hours. The reaction was then quenched with ice water and extracted with dichloromethane. The organic layer was dried over magnesium sulfate, filtered through silica gel and concentrated to give 5.2 g of crude product. Purification by chromatography using 20% ethyl acetate in hexanes yielded 3.1 g of the desired product as a yellow oil, a 51% yield. $n_D^{25}$ 1.4887.

EXAMPLE 5

5-[Cyano(dihyrdo-3,3-dimethyl-2(3H)-furanylidene)-methyl]-2-(difluoromethyl)-4-(2-methylpropyl)-6-(trifluoromethyl)-3-pyridinecarboxylic acid, methyl ester. A 250-mL round-bottom flask equipped with a mechanical stirrer was charged with 2.0 g (5.7 mmol) 5-(cyanomethyl)-4-(2-methylpropyl)-2-(difluoromethyl)-6-(trifluoromethyl)-3-pyridinecarboxylic acid, methyl ester, prepared as in Example d, above, 95 mL dichloromethane, 0.12 g of benzyltriethylammonium chloride, and 2.4 g (11.3 mmol) of 2,2-dimethyl-4-bromobutyryl chloride. The solution was stirred and 24 mL 50% NaOH was added. Two additional equivalents of acid chloride were added after 15 minutes. No further progress of the reaction was noted so the solution was quenched by pouring into water and extracted with ethyl ether. The organics were washed with water, filtered, and concentrated to give 3.1 g of the desired product as a crude light brown oil. Purification by chromatography using 18% ethyl acetate in hexanes yielded 200 mg of the desired product as an oil, an 8% yield. $n_D^{25}$ 1.4840.

EXAMPLE 6

5-(Cyano-1,3-dioxylan-2-ylidene)methyl]-4-(cyclopropylmehtyl)-2-(difluoromethyl)-6-(trifluoromethyl)-3-pyridinecarboxylic acid, methyl ester. To a solution of 3.0 g (8.6 mmol) 5-(cyanomethyl)-4-(cyclopropylmethyl)-2-(difluoromethyl)-6-(trifluoromethyl)-3-pyridinecarboxylic acid, methyl ester, prepared as in Example c, and 4.8 g (25.6 mmol) 2-bromoethyl chloroformate in 125 mL dichloromethane were added 0.3 g benzyltriethylammonium chloride and 50 mL 50% NaOH. The mixture was stirred vigorously for 30 min. and was then poured into 250 mL ice water. The mixture was extracted with ether and the organic layer was washed with brine, dried over magnesium sulfate, treated with decolorizing carbon, and filtered through silica gel. The filtrate was evaporated in vacuo and the residue was chromatographed (HPLC, 50% ethyl acetate/hexane) to yield 1.8 g of the desired product as white crystals following recrystallization from ethyl acetate/hexane, a yield of 50%. m.p. 143°-143.5° C.

EXAMPLE 7

5-[Cyano(dihyrdo-2(3H)-furanylidene)methyl]-2-(difluoromethyl)-4-methyl-6-(trifluoromethyl)-3-pyridinecarboxylic acid, methyl ester. To a solution of 7.00 g (22.7 mmol) 5-(cyanomethyl)-2-(difluoromethyl)-4-methyl-6-(trifluoromethyl)-3-pyridinecarboxylic acid, methyl ester, prepared as in Example E, in 450 mL dichloromethane was added 6.41 g (45.4 mmol) 4-chlorobutyryl chloride, 0.30 g benzyltriethylammonium chloride, and 135 mL 50% sodium hydroxide. The mixture was stirred for 30 minutes, poured over ice, and extracted with diethyl ether. The organic layer was dried with magnesium sulfate, treated wit decolorizing carbon, filtered through silica gel, and evaporated in vacuo. The residue was recrystallized in ethyl acetate and hexane, yielding 4.59 g of the desired product as a white crystalline solid, a 54% yield. m.p. 160°-161° C.

EXAMPLE 8

2-(Difluoromethyl)-5-[(3-chlorodihydro-2(3H)-furanylidene) cyanomethyl]-6-(trifluoromethyl)-4-(2-methylpropyl)-3-pyridinecarboxylic acid, methyl ester. A 100 mL round-bottomed flask was charged with 1.2 g (2.9 mmol) of the compound of Example 2 and 30 mL anhydrous THF and cooled to −70° C. Then 2.9 mL sodium bis(trimethylsilyl)amide (1.0 M solution in THF) was added. After 5 minutes, 0.48 g (2.9 mmol) trifluoromethanesulfonyl chloride was added. To the reaction mixture was added 0.25 g additional trifluoromethanesulfonyl chloride. The reaction mixture was poured into dilute HCl and extracted with ethyl ether. The combined organic layers were dried over magnesium sulfate, filtered and concentrated to give 1.3 g of crude product. Chromatography using 15% ethyl acetate in hexanes yielded 0.34 g of the desired product, as a yellow oil, a 27% yield. $n_D^{25}$ 1.4860.

EXAMPLES 9-11

2-(Difluoromethyl)-5-[(3-chlorodihydro-2(3H)-furanylidene)cyanomethyl]-6-(trifluoromethyl)-4-(2-methylpropyl)-3-pyridinecarboxylic acid, methyl ester, of Example 8 was reacted with a nucleophile to achieve substitution for the chloro radical (R') and produce the following compounds:

| Ex. No. | Reactant | Compound Name | Phys. Property |
|---|---|---|---|
| 9 | NaSCH₃ | 5-[Cyano[dihydro-3-(methylthio)-2(3H)furanylidene]-methyl]-2-(difluoromethyl)-4-(2-methylpropyl)-6-(trifluoromethyl)-3-pyridinecarboxylic acid, methyl ester | $n_D^{25}$ 1.5103 |
| 10 | NaCN | 5-[Cyano[3-cyanodihydro-2(3H)-furanylidene]-methyl]-2-(difluoromethyl)-4-(2-methylpropyl)-6-(trifluoromethyl)-3-pyridinecarboxylic acid, methyl ester | m.p. 119–121° C. |
| 11 | OH⁻ | 5-[Cyano(dihydro-3-hydroxy-2(3H)-furanylidene)methyl]-2-(difluoromethyl)-4-(2-methylpropyl)-6-(trifluoromethyl)-3-pyridinecarboxylic acid, methyl ester | |

EXAMPLE 12

5[Cyano(3,3-dichlorodihydro-2(3H)-furanylidene)-methyl]-2-(difluoromethyl)-4-(2-methylpropyl)-6-(trifluoromethyl)-3-pyridinecarboxylic acid, methyl ester. A 100 mL round-bottomed flask was charged with 1.5 g (3.6 mmol) of the compound of Example 2 and 20 mL anhydrous THF. The solution was cooled to −70° C. and 3.6 mL sodium bis(trimethylsilyl)amide (1.0 M solution in THF) was added via syringe. After 5 minutes, 0.6 g (3.6 mmol) trifluoromethanesulfonyl chloride was added. After 15 minutes an additional 3.6 mL sodium bis(trimethylsilyl)amide was added followed by additional 0.6 g trifluoromethanesulfonyl chloride. After stirring one hour at −70° C., the reaction solution was poured into dilute HCl and extracted with ethyl ether. The combined organic layers were washed with brine, dried over magnesium sulfate, an filtered to give 1.5 g of crude orange oil. Chromatography using 20% ethyl acetate in hexanes yielded 0.42 g of the desired product as a yellow oil, a 24% yield. $n_D^{25}$ 1.4920.

EXAMPLE 13

4-(Cyclopropylmethyl)-2-(difluoromethyl)-5-(2-dithiolanylidenemethyl)-6-(trifluoromethyl)-3-pyridinecarboxylic acid, methyl ester. To a suspension of 5.9 g (13.0 mmol) of (2-dithiolanyl)triphenylphosphonium tetrafluoroborate in 125 mL anhydrous THF at −50° C. was addd 5.2 mL (13.0 mmol) n-butyllithium (2.5 M in hexane). After stirring for 30 min at −50° C., a solution of 4.0 g (11.9 mmol) of the 5-formyl-3-pyridinecarboxylic acid, methyl ester, prepared as in Example b, in 10 mL THF was added dropwise. The mixture was allowed to warm to room temperature and then poured into 5% aqueous NH₄Cl and extracted with ethyl ether. The organic layer was washed with brine, dried over magnesium sulfate, and filtered through silica gel. The filtrate was evaporated in vacuo to yield a crude product which when purified by HPLC (15% ethyl acetate/hexane) yielded 4.3 g of the desired product as white crystals, an 86% yield. m.p. 86°–87° C.

EXAMPLE 14

4-(Cyclopropylmethyl)-2-(difluoromethyl)-5-(1,3-oxathiolan-2-ylidenemethyl)-6-(trifluoromethyl)-3-pyridinecarboxylic acid, methyl ester. The 5-formyl-3-pyridinecarboxylic acid, methyl ester, prepared as in Example b, 2.2 g (6.5 mmol) was reacted with 3.2 g (6.5 mmol) [2-(1,3-oxathiolane)yl]triphenylphosphonium tetrafluoroborate using the method of Example 13 to yield a crude product which when purified by HPLC (15% ethyl acetate/hexane) yielded 0.5 g of the desired product as a colorless oil, a 19% yield. $n_D^{25}$ 1.5181.

EXAMPLE 15

2-(Difluoromethyl)-5-(1,3-dithiolan-2-ylidenemethyl)-4-(2-methylpropyl)-6-(trifluoromethyl)-3-pyridinecarboxylic acid, methyl ester. To a suspension of 3.75 g (8.5 mmol) 1,3-dithiolan-2-yltriphenylphosphonium tetrafluoroborate in 50 mL anhydrous THF at −70° C. was added 3.4 mL n-butyllithium (2.5 M solution. After stirring for 5 minutes, a solution of 2.62 g (7.7 mmol) of the 5-formyl-3-pyridinecarboxylic acid, methyl ester, prepared as in Example a, in 25 mL THF was added dropwise. The reaction mixture was stirred for 15 minutes at −70° C. and then allowed to reach room temperature. After one hour the solution was poured into cold 1.2 M HCl and extracted with ethyl ether. The organic phase was washed with brine, dried over magnesium sulfate, filtered, and concentrated to give 3.9 g of crude product. Purification by chromatography using 15% ethyl acetate in hexanes yielded 2.16 g of the desired product, as a light yellow oil, a yield of 67%. $n_D^{25}$ 1.5172.

EXAMPLE 16

2-(Difluoromethyl)-5-(1,3-oxathiolan-2-ylidenemethyl)-4-(2-methylpropyl)-6-(trifluoromethyl)-3-pyridinecarboxylic acid, methyl ester. The method of Example 15, substituting 1,3-oxathiolan-2-yltriphenylphosphonium tetrafluoroborate for the tetrafluoroborate therein, produced the desired product as a light yellow oil in a 33% yield. $n_D^{25}$ 1.4944.

EXAMPLE 17

4-(Cyclopropylmethyl)-2-(difluoromethyl)-5-[(dihydro-2(3H)-furanylidenemethyl)-6-(trifluoromethyl)-3-pyridinecarboxylic acid, methyl ester. To a solution of 1.6 g (15.8 mmol) diisopropylamine in 60 mL dry THF cooled to −70° C. was added 6.2 mL (15.5 mmol) n-butyllithium (2.5 M in hexanes). The mixture was allowed to warm to 0° C. and was cooled back to 31 70° C. To the resulting solution was added a solution of 4.2 g (15.4 mmol) of diphenyl-2-tetrahydrofuranylphosphine oxide in 35 mL dry THF. The mixture was stirred at −70° C. for 15 min and to the dark red solution was added 5.0 g of the compound of Example b in 15 mL dry THF. The mixture was allowed to warm to room temperature and was allowed to stir for 16 hours. The mixture was cooled on an ice bath and to the mixture was added 100 mL of 1.2 M HCl. The organic layer was washed with brine, dried over magnesium sulfate, and filtered through silica gel. The filtrate was evaporated in vacuo and the residue was chromatographed (HPLC, 10% ethyl acetate/hexane) to yield 2.5 g of the desired product as a colorless oil, a 47% yield. $n_D^{25}$ 1.4907.

EXAMPLE 18

4-(Cyclopropylmethyl)-2-(difluoromethyl)-5-(1-methyl-2-pyrrolidinylidene)-6-(trifluoromethyl) -3-pyridinecarboxylic acid, methyl ester. Using the method of Example 17, substituting diphenyl(1-methyl-2-pyrrolidinyl)phospine oxide for the phosphine oxide therein produced the desired product as a yellow liquid in a 31% yield. $n_D^{25}$ 1.5047.

EXAMPLE 19

5-(Cyclopentylidenemethyl)-2-(difluoromethyl)-4-(2-methylpropyl)-6-(trifluoromethyl)-3-pyridinecarboxylic acid, methyl ester. A solution of 10.0 g (29.4 mmol) of the 5-formyl-3-pyridinecarboxylic acid, methyl ester, prepared as in Example a, in 100 mL anhydrous THF was cooled to 0° C. and 14.8 mL cyclopentylmagnesium chloride (2.0 M solution) was added via syringe. Additional cyclopentylmagnesium chloride solution was added until no starting material was observed by GC. The reaction mixture was quenched with dilute HCl and extracted twice with ethyl ether. The combined organic layers were dried over magnesium sulfate, filtered, and concentrated to give 11.2 g of crude yellow-orange oil. Chromatography using 5% ethyl acetate in hexanes gave 2.2 g of the cyclopentyl alcohol derivative, a 20 % yield. A solution of 2.1 g (5.1 mmol) of the cyclopentyl alcohol in 50 mL toluene was charged in a round bottomed flask. Four equivalents (0.70 g) of phosphorus pentoxide were added. The solution was refluxed and additional phosphorus pentoxide was added until no starting material was observed by GC. The solution was partitioned between aqueous sodium bicarbonate and ethyl ether. The combined organic layers were washed with brine, dried over magnesium sulfate, filtered, and concentrated to give 2.2 g of crude product. Chromatography using 5% ethyl acetate in hexanes yielded 420 mg of the desired product as an oil, a 21% yield. $n_D^{25}$ 1.4771.

EXAMPLE 20

5-(2-Bromo-2-cyclopentylidenemethyl)-2-(difluoromethyl)-4-(2-methylpropyl)-6-(trifluoromethyl) -3-pyridinecarboxylic acid, methyl ester. To a solution of 4.5 g (11.5 mmol) of the compound of Example 19 in 75 mL of CCl4 was added 2.0 g (12.5 mmol) bromine. The mixture was heated to reflux for 20 min and allowed to cool to room temperature. To the mixture was added 3 g triethylamine and the mixture was heated to reflux for another 20 minutes. The mixture was cooled to room temperature and was partitioned between ether and water. The organic layer was washed with brine, dried over magnesium sulfate, and filtered through silica gel. The filtrate was evaporated in vacuo and the residue was chromatographed (HPLC, 5% ethyl acetate/hexane) to yield 0.7 g of the desired product as a colorless oil, a 13% yield. $n_D^{25}$ 1.4955.

EXAMPLE 21

2-(Difluoromethyl)-5-[dihydro-2(3H)-furanylidiene)-methyl]-4-(2-methylpropyl)-6-( trifluoromethyl)-3-pyridinecarboxylic acid, methyl ester. A solution of 5.0 g (11.9 mmol) of the compound of Example 2 in 30 mL conc. $H_2SO_4$ was stirred for 4 days at ambient temperature. TLC showed no starting material so the solution was poured over ice and extracted with ethyl ether. The water phase was extracted twice with 150 mL ethyl acetate and the combined organic layers were dried over magnesium sulfate, filtered, and concentrated to give 2.5 g of a dark purple oil. Chromatography using 50% ethyl acetate in hexanes yielded 1.8 g of the 5-[2-amino-1-(dihydro-b 2(3H)-furanylidene)-2-oxoethyl]-derivative, as an off white solid, a 35% yield. m.p. 185°–186° C.

This reaction was repeated to obtain 4.7 g (10.8 mmol) of this amide which was dissolved in 20 mL 1,4-dioxane. To this solution was added 20 mL conc. HCl. The mixture was heated to reflux for 4 days and was partitioned between ether and water. The aqueous layer was extracted with another two portions of ether and the ether layers were combined. The organic phase was dried over magnesium sulfate and filtered. The filtrate was evaporated in vacuo and the residue was chromatographed (HPLC, 15% ethyl acetate/hexane) to yield 2.1 g of a colorless oil, a 47% yield.

A portion of this compound, 1.7 g (4.1 mmol), in 25 mL methylene chloride was stirred with 0.1 g benzyltriethylammonium chloride and 12 mL of 50% NaOH. The reaction mixture was stirred at ambient temperature for 20 minutes. The solution was poured over ice water and extracted twice with 100 mL ethyl ether. The organics were dried over magnesium sulfate, filtered, and concentrated to give 1.6 g of crude product. Chromatography using 10% ethyl acetate in hexanes afforded 1.1 g of the title compound, as a clear colorless oil, a yield of 67%. $n_D^{25}$ 1.4711.

EXAMPLE 22

5-[Cyano(dihydro-2(3H)-furanylidene)methyl]-2-(difluoromethyl)-4-(2-methylpropyl)-6-(trifluoromethyl)-3-pyridinecarboxylic acid. To a solution of 10.0 g (23.9 mmol) of the compound of Example 2 in 100 mL methanol were added 14.7 g (223 mmol) KOH pellets (85%). The mixture was stirred at room temperature for 3 days and was then partitioned between ether and water. The aqueous layer was acidified with conc. HCl and extracted with ether. The ether layer was washed with brine, dried over magnesium sulfate, and filtered. The filtered. The filtrate was evaporated in vacuo and the residue was recrystallized from ethyl acetate/hexane to yield 8.9 g of the desired product as white crystals, a 93% yield. m.p. 192°–193° C.

EXAMPLE 23

5-[Cyano(dihydro-2-(3H)-furanylidene)methyl]-2-(difluoromethyl)-4-(2-methylpropyl)-6-(trifluoromethyl)-3-pyridinecarbothioic acid, S-methyl ester. To a solution of 10.62 g (26.3 mmol) of the compound of Example 22 in 60 mL thionyl chloride was added 0.5 mL pyridine as a catalyst. The mixture was stirred overnight at room temperature and then heated to reflux for 2 hours. Excess thionyl chloride was removed in vacuo and the mixture was partitioned between diethyl ether and water. The organic layer was washed with brine, dried over magnesium sulfate, and filtered. The filtrate was evaporated in vacuo, yielding 8.29 g of the acid chloride derivative as a dark yellow oil a 75% yield.

To a solution of 2.00 g (4.7 mmol) of this 3-pyridinecarboxylic acid chloride in 40 mL anhydrous THF was added 0.40 g (5.7 mmol) sodium methanethiolate. The mixture was stirred at reflux for 15 minutes and was partitioned between ether and water. The organic layer was washed with 10% sodium hydroxide and then with brine, dried with magnesium sulfate, filtered through silica gel, and the filtrate evaporated in vacuo. The residue was kugelrohr distilled, yielding 0.70 g of the desired product as a yellow oil, a 34% yield. $n_D^{25}$ 1.15190.

This 3-pyridinecarboxylic acid chloride was reacted with a nucleophile to achieve substitution for the chloro radical to produce the following compounds.

| Ex. No. | Reactant | Compound Name | Phys. Property |
|---|---|---|---|
| 24 | Propargyl alcohol | 5-[Cyano(dihydro-2(3H)-furanylidene)methyl]-2-(difluoromethyl)-4-(2-methylpropyl)-6-(trifluoromethyl)-3-pyridinecarboxylic acid, 2-propynyl ester | m.p. 78–79° C. |
| 25 | Diethylamine | 5-[Cyano(dihydro-2(3H)-furanylidene)methyl]-N,N-diethyl-2-(difluoromethyl)-4-(2-methylpropyl)-6-(trifluoromethyl)-3-pyridinecarboxamide | m.p. 116–117° C. |
| 26 | Ethanol | 5-[Cyano(dihydro-2(3H)-furanylidene)methyl]-2-(difluoromethyl)-4-(2-methylpropyl)-6-(trifluoromethyl)-3-pyridinecarboxylic acid, ethyl ester | $n_D^{25}$ 1.4906 |
| 27 | Allyl alcohol | 5-[Cyano(dihydro-2(3H)-furanylidene)methyl]-2-(difluoromethyl)-4-(2-methylpropyl)-6-(trifluoromethyl)-3-pyridinecarboxylic acid, 2-propenyl ester | $n_D^{25}$ 1.0630 |
| 28 | Aniline | 5-[Cyano(dihydro-2(3H)-furanylidene)methyl]-2-(difluoromethyl)-4-(2-methylpropyl)-N-phenyl-6-(trifluoromethyl)-3-pyridinecarboxamide | m.p. 178–179° C. |
| 29 | 2-Fluoro-ethanol | 5-[Cyano(dihydro-2(3H)-furanylidene)methyl]-2-(difluoromethyl)-4-(2-methylpropyl)-6-(trifluoromethyl)-3-pyridinecarboxylic acid, fluoroethyl ester | $n_D^{25}$ 1.4895 |
| 30 | n-Butylamine | N-Butyl-5-[cyano(dihydro-2(3H)-furanylidene)methyl]-2-(difluoromethyl)-4-(2-methylpropyl)-6-(trifluoromethyl)-3-pyridinecarboxamide | m.p. 160° C. |

EXAMPLE 31

5-[Cyano(dihydro-2-(3H)-furanylidene)methyl]-2-(difluoromethyl)-4-(2-methylpropyl)-6-(trifluoromethyl)-3-pyridinecarboxylic acid, methyl ester. To a solution of 10.0 g (23.9 mmol) of the compound of Example 2 in 200 mL dichloromethane was added 9.6 g (71.9 mmol) aluminum chloride. The mixture was stirred at ambient for 1.5 hours and was poured into water. To this mixture was added conc. HCl and the mixture was extracted with ether. The organic layer was washed with aqueous NaHCO$_3$ followed by brine. The ether layer was dried over magnesium sulfate, filtered through silica gel, and the filtrate was evaporated in vacuo. The residue was chromatographed (35% ethyl acetate/hexane) to yield 6.5 g of the desired product as a light yellow oil, a 60% yield. $n_D^{25}$ 1.5807.

EXAMPLE 32

5-[Cyano(dihydro-2(3H)-furanylidine)methyl]-2-dimethoxymethyl)-4-(2-methylpropyl)-6-(trifluoromethyl)-3-pyridinecarboxylic acid, methyl ester. To a solution of 2.0 g (4.4 mmol) of the compound of Example 31 in 30 mL methanol was added 4.0 g (18.5 mmol) 25% sodium methoxide in methanol. The mixture was heated to reflux for 18 hours and was allowed to cool to room temperature. The mixture was partitioned between ether and dilute HCl. The organic layer was washed with brine, dried over magnesium sulfate, and filtered through silica gel. The filtrate was evaporated in vacuo and the residue was chromatographed (HPLC, 40% ethyl acetate/hexane) to yield 1.1 g of the desired product as a light yellow oil, a 56% yield. $n_D^{25}$ 1.4950.

EXAMPLE 33

5-[Cyano(dihydro-2(3H)-furanylidine)methyl]-2-methyl-4-(2-methylpropyl)-6-(trifluoromethyl)-3-pyridinecarboxylic acid, methyl ester. To a solution of 3.0 g (6.7 mmol) of the compound of Example 31 in 30 mL methanol was added 0.5 g of 5% palladium on carbon/ 50% H$_2$O and 6 g triethylamine. The mixture was subjected to 54 psi of hydrogen for 30 min. and was then filtered through silica gel. The filtrate was evaporated in vacuo and the residue was partitioned between ether and water. The organic layer was dried over magnesium sulfate, filtered through silica gel, and the filtrate was evaporated in vacuo. The residue was chromatographed (HPLC, 35% ethyl acetate/hexane) to yield 1.6 g of the desired product as a light yellow oil, a 64% yield. $n_D^{25}$ 1.5056.

EXAMPLE 34

5-[Cyano(dihydro-2(3H)-furanylidine)methyl]-2-chloromethyl)-4-(2-methylpropyl)-6-(trifluoromethyl)-3-pyridinecarboxylic acid, methyl ester. To a mixture of 5% palladium on carbon/ 50% H$_2$O in 30 mL methanol was added 13.9 g (30.8 mmol) of the compound of Example 31 and 3.1 g (31.0 mmol) triethylamine. The mixture was subjected to 53 psi of hydrogen for 2.5 hours. The mixture was then filtered through silica gel and the filtrate was partitioned between diethyl ether and water. The organic layer was dried with magnesium sulfate, filtered through silica gel, and evaporated in vacuo. The residue was chromatographed (HPLC, 30% ethyl acetate/hexane), yielding 10.9 g of the desired product as of a yellow oil, an 85% yield. $n_D^{25}$ 1.5160.

EXAMPLE 35

5-[Cyano(dihydro-2(3H)-furanylidine)methyl]-6-(difluoromethyl)-4-[(methylthio)methyl]-2-(trifluoromethyl)-3-pyridinecarboxylic acid, ethyl ester. To a solution of 29.3 g (78.6 mmol) of the pyridine prepared as in Example 158 of U.S. Pat. No. 4,692,184 in 250 mL anhydrous THF was added 157 mL (157 mmol) borane-THF complex (1.0 M in THF). The mixture was stirred at room temperature for 6 days and was quenched with 250 mL 2.4 M HCl. The mixture was extracted with ether and the organic layer was washed with 10% NaOH followed by brine. The organic layer was filtered through silica gel and the filtrate was evaporated in vacuo to yield 20.6 g of the 5-hydroxymethyl derivative as a yellow oil. An analytical sample was chromatographed (HPLC, 15% ethyl acetate/hexane) to give a colorless oil which crystallized on standing. The product was recrystallized to give white crystals. m.p. 70.5°–71° C.

To a solution of 13.5 g (37.6 mmol) of this pyridine alcohol in 150 mL carbon tetrachloride was added 10.3 g (39.3 mmol) triphenylphosphine. The mixture was heated to reflux for 26 hours and was allowed to cool to room temperature. The mixture was filtered through silica gel and the filtrate was evaporated in vacuo. The residue was dissolved in hexane and filtered through silica gel. The filtrate was evaporated in vacuo and the residue was chromatographed (HPLC, 5% ethyl acetate/hexane) to yield 8.1 g of the 5-chloromethyl derivative as a colorless oil, a 57% yield.

To a solution of 7.9 g (20.9 mmol) of the 5-chloromethyl pyridine thus produced in 150 mL anhydrous DMF was added 1.1 g (22.4 mmol) finely powdered sodium cyanide. The mixture was stirred on an ice bath for 45 minutes and was then poured into ice-water and extracted with ether. The organic layer was washed with two portions of water followed by brine, drive over magnesium sulfate, and filtered through silica gel. The filtrate was evaporated in vacuo and the residue amounted to 7.5 g of a brown oil. The crude product mixture was dissolved in 400 mL methylene chloride and to the mixture was added 2.3 g (16.3 mmol) 4-chlorobutyryl chloride, 0.2 g benzyltriethylammonium chloride, and 300 mL 50% NaOH. The mixture was stirred at ambient temperature for 20 minutes and another 2.3 g (16.3 mmol) 4-chlorobutyryl chloride was added dropwise. Stirring was continued for another 2 hours and the mixture was poured into ice-cold water and ether. The organic layer was separated and washed with brine. The ether phase was dried over magnesium sulfate, treated with decolorizing carbon, and filtered through silica gel. The filtrate was evaporated in vacuo and the residue was chromatographed (HPLC, 50% ethyl acetate/hexane) to yield 1.7 g of the desired product as a yellow oil, a 71% yield. $n_D^{25}$ 1.5179.

EXAMPLE 36

5-[Cyano(dihydro-2(3H)-furanylidine)methyl]-6-(difluoromethyl)-4-iodomethyl-2-(trifluoromethyl)-3-pyridinecarboxylic acid, ethyl ester. To a solution of the compound of Example 35 in 50 mL anhydrous acetonitrile was added 1.4 g (7.1 mmol) silver tetrafluoroborate and 1.5 g (10.6 mmol) methyl iodide. The mixture was heated to reflux for 4.5 hours and was filtered. The filtrate was evaporated in vacuo and the residue amounted to 4.0 g of the 4-[(dimethylsulfenyl)methyl)]-derivative as a brown foam.

This residue (7.4 mmol) was dissolved in 40 mL acetone and 1.7 g (11.3 mmol) sodium iodide was added. The mixture was stirred at room temperature for 18 hours and then heated to reflux for 3 hours. The solvent was removed in vacuo and the residue was partitioned between ether and water. The organic layer was washed with brine, dried over magnesium sulfate, and treated with decolorizing carbon. The mixture was filtered through silica gel and the filtrate was evaporated in vacuo to give a yellow solid. The solid product was recrystallized from ethyl acetate/hexane to yield 2.3 g of the desired product as white crystals, a 60% yield. m.p. 142°–143° C.

EXAMPLE 37

5-[Cyano(dihydro-2(3H)-furanylidine)methyl]-6-(difluoromethyl)-4-[dimethylamino)methyl]-2-(trifluoromethyl)-3-pyridinecarboxylic acid, ethyl ester. To a solution of 0.7 g (1.3 mmol) of the compound of Example 36 in 25 mL anhydrous THF was added 1.0 g (8.9 mmol) aqueous dimethylamine. The mixture was stirred at room temperature for 30 minutes and was then partitioned between ether and dilute HCl. The aqueous layer was neutralized with NaHCO$_3$ and extracted with ether. The organic phase was washed with brine, dried over magnesium sulfate, and filtered through silica gel. The filtrate was evaporated in vacuo to yield 0.32 g of the desired product as a colorless oil, a 54% yield. $n_D^{25}$ 1.4947.

EXAMPLE 38

6-(Difluoromethyl)-α-(dihydro-2(3H)-furanylidine)-5-(methoxycarbonyl)-4-(2-methylpropyl)-2-(trifluoromethyl)-3-pyridineacetic acid, methyl ester. To a solution of 4.3 g (9.9 mmol) of the 5-[2-amino-1-(dihydro-2(3H)-furanylidene)-2-oxoethyl]pyridine derivative, prepared as in the first step of Example 21, in 70 mL methanol was added 5.0 g (75.9 mmol) potassium hydroxide pellets (85%). The mixture was heated to reflux for 3 days and was then stirred at room temperature for 2 days. The solvent was removed in vacuo. The residue was partitioned between ether and dilute HCl. The organic layer was washed with brine, dried over magnesium sulfate, and filtered. The filtrate was evaporated in vacuo and the residue was recrystallized from ethyl acetate/hexane to yield 3.7 g (88%) of the free diacid as white crystals. m.p. 218°–219° C.

To a solution of 3.1 g (7.3 mmol) of this diacid in 20 mL thionyl chloride were added several drops of pyridine. The mixture was stirred at room temperature for 19 hours and was concentrated in vacuo. The residue was partitioned between ether and water. The organic layer was washed with brine, dried over magnesium sulfate, and filtered. The filtrate was evaporated in vacuo and the product was recrystallized from ethyl acetate/hexane to yield 3.0 g of the diacid chloride derivative as white crystals, a yield of 88%. m.p. 92.5°–93° C.

To 2.0 g (4.3 mmol) of the diacid chloride was added 20 mL methanol. The mixture was stirred at room temperature for 1.5 hours and then at reflux for 45 minutes. Methanol was removed in vacuo and the residue amounted to 1.95 g of the desired product as a colorless oil, a 100% yield. $n_D^{25}$ 1.4907.

EXAMPLE 39

5-[Cyano(dihydro-2(3H)-furanylidine)methyl]-2-methoxy-4-(2-methylpropyl)-6-(trifluoromethyl)-3-pyridinecarboxylic acid, methyl ester. To a solution of 28.5 g (83.9 mmol) of the compound prepared as in Example f in 250 mL DMF was added 4.9 g (100 mmol) sodium cyanide. After stirring for 0.5 hours, the 5-cyanomethyl derivative was isolated and purified by kugelrohr distillation as 25.4 g white crystals, a 92% yield. m.p. 66°–67° C.

This 5-cyanomethyl-3-pyridinecarboxylic acid, methyl ester (5.0 g, 15.1 mmol) was converted to the desired product by reaction with 3.1 g (16.7 mmol) 4-bromobutyryl chloride and lithium diisopropylamide in THF. Purified product was obtained following HPLC (20% ethyl acetate/hexane) as 3.9 g of a colorless oil, a 65% yield. $n_D^{25}$ 1.5027.

HERBICIDAL EFFICACY EXAMPLES

Pre-Emergent Activity on Plants

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0-24 | 0 |
| 25-49 | 1 |
| 50-74 | 2 |
| 75-100 | 3 |
| Not planted | — or a blank |
| Species planted, no data | N |

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha). After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed diagonally above the columns according to the following legend:

| |
|---|
| CATH—Canada thistle* |
| RHQG—Quackgrass* |
| COBU—Cocklebur |
| RHJG—Rhizome Johnsongrass* |
| VELE—Velvetleaf |
| DOBR—Downy Brome |
| MOGL—Morningglory |
| BYGR—Barnyardgrass |
| COLQ—Common Lambsquarters |
| ANBG—Annual Bluegrass |
| PESW—Pennsylvania Smartweed |
| SEJG—Seedling Johnsongrass |
| YENS—Yellow Nutsedge* |
| INMU—Indian Mustard |
| WIBW—Wild Buckwheat |

*Grown from vegetative propagules

TABLE A

Herbicide Primary Pre, spectrums 25 and 90
(C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 90 | C | C | 90 | C | 90 | 90 | C | C | C | — | — | — | — | — |
| 2 | 11.2100 | 90 | C | C | 90 | C | 90 | 80 | C | C | C | — | — | — | — | — |
| 3 | 11.2100 | 90 | C | C | 90 | C | 90 | 10 | 90 | C | 80 | — | — | — | — | — |
| 4 | 11.2100 | 70 | C | C | 90 | C | C | 80 | 90 | C | 90 | — | — | — | — | — |
| 5 | 11.2100 | 0 | C | C | 90 | C | 70 | 20 | 80 | C | 90 | — | — | — | — | — |
| 6 | 11.2100 | 50 | C | 90 | 30 | C | 40 | 0 | 80 | 90 | 80 | — | — | — | — | — |
| 7 | 11.2100 | 0 | C | C | 30 | C | 70 | 10 | C | C | 90 | — | — | — | — | — |
| 8 | 11.2100 | 20 | C | 80 | C | C | 60 | 20 | 80 | C | 90 | — | — | — | — | — |
| 9 | 11.2100 | 0 | C | 80 | 90 | C | 60 | 30 | 70 | C | 80 | — | — | — | — | — |
| 10 | 11.2100 | 10 | 90 | 70 | 0 | C | 10 | 0 | 40 | 90 | 50 | — | — | — | — | — |
| 11 | 11.2100 | 50 | C | C | 70 | C | 90 | 70 | C | C | 90 | — | — | — | — | — |
| 12 | 11.2100 | 0 | C | 90 | 90 | C | 50 | 40 | 80 | C | 70 | — | — | — | — | — |
| 13 | 11.2100 | 0 | C | C | 70 | C | 70 | 0 | 60 | C | 20 | — | — | — | — | — |
| 14 | 11.2100 | 60 | C | C | 90 | C | 80 | 60 | 90 | C | 90 | — | — | — | — | — |
| 15 | 11.2100 | 0 | C | C | 80 | C | 80 | 10 | 80 | 90 | 90 | — | — | — | — | — |
| 16 | 11.2100 | 10 | C | C | 90 | C | 80 | 10 | 90 | C | C | — | — | — | — | — |
| 17 | 11.2100 | C | C | C | C | C | 90 | 40 | 90 | C | 90 | — | — | — | — | — |
| 18 | 11.2100 | 40 | C | C | 90 | C | 70 | 10 | 60 | C | 40 | — | — | — | — | — |
| 19 | 11.2100 | 30 | C | C | C | C | 90 | 60 | 90 | C | 90 | — | — | — | — | — |
| 20 | 11.2100 | 30 | C | C | 90 | C | 80 | 40 | 80 | C | 90 | — | — | — | — | — |
| 21 | 11.2100 | 90 | C | C | 90 | C | 90 | 80 | C | C | 90 | — | — | — | — | — |
| 22 | 11.2100 | 0 | 0 | 0 | 0 | 0 | 0 | 0 | 0 | 0 | 0 | — | — | — | — | — |
| 23 | 11.2100 | 50 | C | 90 | 90 | C | 90 | 80 | 90 | C | 80 | — | — | — | — | — |
| 24 | 11.2100 | 80 | C | C | 80 | C | 80 | 40 | 80 | C | 80 | — | — | — | — | — |
| 25 | 11.2100 | 0 | 80 | 90 | 30 | C | 40 | 0 | 30 | 60 | 70 | — | — | — | — | — |
| 26 | 11.2100 | 50 | C | C | 70 | C | 70 | 50 | 80 | C | C | — | — | — | — | — |
| 27 | 11.2100 | 0 | C | C | 40 | C | 40 | 10 | 80 | C | C | — | — | — | — | — |
| 28 | 11.2100 | 0 | N | 20 | 0 | 0 | 0 | 0 | 0 | 0 | 0 | — | — | — | — | — |
| 29 | 11.2100 | 40 | C | C | 70 | C | 80 | 10 | 80 | C | 90 | — | — | — | — | — |
| 30 | 11.2100 | 0 | 0 | 0 | 0 | 0 | 0 | 0 | 0 | 0 | 0 | — | — | — | — | — |
| 31 | 11.2100 | 70 | C | 90 | 90 | C | 70 | 50 | C | C | C | — | — | — | — | — |
| 32 | 11.2100 | 90 | C | C | C | C | 80 | 70 | C | C | C | — | — | — | — | — |
| 33 | 11.2100 | C | C | C | C | C | 90 | 80 | C | C | C | — | — | — | — | — |
| 34 | 11.2100 | 0 | C | 80 | 20 | C | 30 | 0 | 70 | C | 60 | — | — | — | — | — |
| 35 | 11.2100 | 0 | C | C | 60 | C | 80 | 10 | 70 | C | 50 | — | — | — | — | — |

TABLE A-continued

Herbicide Primary Pre, spectrums 25 and 90
(C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 36 | 11.2100 | 0 | 80 | 20 | 0 | 20 | 0 | 0 | 0 | 0 | 0 | — | — | — | — | — |
| 37 | 11.2100 | 0 | 80 | 80 | 20 | 80 | 30 | 0 | 0 | 80 | 50 | — | — | — | — | — |
| 38 | 11.2100 | C | C | C | 90 | C | C | 30 | 80 | C | C | — | — | — | — | — |
| 39 | 11.2100 | 40 | C | C | 90 | C | 90 | 70 | 90 | C | 90 | — | — | — | — | — |

In another set of tests, the pre-emergence activity of compounds of this invention was tested on weeds in the presence of crop plants. In these tests the following procedure was used:

Topsoil was sieved to pass through a 1.27 cm screen. Fertilizer was added to the topsoil in some of the tests, while in testing other compounds the fertilizer was omitted. The mixture was then sterilized by exposure to methyl bromide or by heating.

The topsoil mixture was placed in individual aluminum pans and compacted to a depth of about 1.27 cm. from the top of the pan. A predetermined number of seeds of each of several monocotyledonous and dicotyledonous plant species and, where noted, vegetative propagules of various perennial plant species were slanted in the pans. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. In Table B below the amount of active ingredient applied is shown. After treatment, the pans were moved to a greenhouse bench. Moisture was supplied to each pan as needed for germination and growth. Growth of each species was observed and corrective measures (greenhouse fumigation, insecticide treatment, and the like) were applied as needed. Approximately 10–14 days (usually 11 days) after planting and treating, the plants were observed and the results recorded.

The pre-emergence data for weeds in the presence of crop plants are shown in the following Table B. In these tests, the plants are identified according to the following column headings.

| | |
|---|---|
| SOBE—Soybean | VELE—Velvetleaf |
| SUBE—Sugarbeet | DOBR—Downy Brome |
| WHEZ—Wheat | PRMI—Proso Millet |
| RICE—Rice | BYGR—Barnyardgrass |
| GRSO—Grain Sorghum | LACG—Large Crabgrass |
| COBU—Cocklebur | GRFT—Green Foxtail |
| WIBW—Wild Buckwheat | CORN—Corn |
| MOGL—Morningglory | COTZ—Cotton |
| HESE—Hemp Sesbania | RAPE—Oilseed Rape |
| COLQ—Common Lambsquarters | JIWE—Jimsonweed |
| PESW—Pennsylvania Smartweed | COCW—Common Chickweed |
| ANBG—Annual Bluegrass | RUTH—Russian Thistle |
| BARZ—Barley | SEJG—Seedling Johnsongrass |
| WIOA—Wild Oats | |

TABLE B

Herbicide Secondary Pre, spectrums 26, 88, 91, 93, 95, 96, and 100
(C = 100% control)

| Ex. No. | Rate kg/ha | Sobe | Cotz | Rape | Cobu | Wibw | Mogl | Hese | Jiwe | Vele | Whez | Rice | Grso | Corn | Dobr | Prmi |
|---|---|---|---|---|---|---|---|---|---|---|---|---|---|---|---|---|
| 1 | 5.6050 | 95 | 85 | 95 | 80 | 90 | 95 | 95 | 90 | 95 | C | C | C | 95 | C | C |
|   | 1.1210 | 99 | 20 | 95 | 75 | 95 | 95 | 90 | 80 | 90 | 98 | 99 | C | 98 | C | C |
|   | 0.2803 | 75 | 10 | 85 | 20 | 90 | 65 | 70 | 85 | 90 | 90 | 95 | 95 | 85 | 95 | C |
|   | 0.0701 | 25 | 30 | 90 | 0 | 90 | 0 | 70 | 75 | 80 | 75 | 75 | 90 | 35 | 90 | 75 |
|   | 0.0175 | 20 | 0 | 35 | 0 | 0 | 0 | 0 | 70 | 0 | 0 | 35 | 0 | 15 | 90 | 60 |
|   | 0.0087 | 25 | N | 0 | 0 | 0 | 0 | 0 | 30 | 0 | 30 | 25 | 0 | 0 | 90 | 50 |
| 2 | 5.6050 | 99 | C | C | 75 | C | C | C | — | C | C | C | C | C | C | C |
|   | 1.1210 | 95 | 90 | C | 75 | C | C | 95 | — | C | C | 98 | C | 95 | C | C |
|   | 0.2803 | 98 | 85 | C | 65 | C | 90 | 98 | — | C | 95 | 95 | C | 95 | 95 | C |
|   | 0.0701 | 90 | 35 | 99 | 40 | 95 | 85 | 95 | — | C | 90 | 85 | C | 90 | C | C |
|   | 0.0175 | 70 | 0 | 99 | 0 | 70 | 25 | 65 | — | 85 | 75 | 70 | 95 | 90 | 75 | C |
|   | 0.0087 | 65 | 15 | 90 | 0 | 35 | 45 | 55 | — | 80 | 30 | 55 | 65 | 20 | 65 | 90 |
| 3 | 5.6050 | 90 | 75 | C | 90 | C | 90 | 90 | — | 95 | 90 | 95 | C | 90 | 85 | C |
|   | 1.1210 | 90 | 0 | 95 | 35 | 95 | 60 | 40 | — | 70 | 85 | 50 | 95 | 90 | 35 | 75 |
|   | 0.2803 | 25 | 20 | 90 | 0 | 95 | 75 | 70 | — | 55 | 30 | 55 | 75 | 35 | 30 | C |
|   | 0.0701 | 35 | 0 | 0 | 0 | 75 | 0 | 0 | — | 0 | 20 | 35 | 0 | 30 | 10 | 50 |
|   | 0.0175 | 0 | 0 | 0 | 0 | 35 | 0 | 0 | — | 0 | 45 | 0 | 0 | 20 | 0 | 30 |
|   | 0.0087 | 10 | 15 | 0 | 0 | 0 | 0 | 0 | — | 0 | 0 | 0 | 0 | 20 | 0 | 0 |
| 4 | 5.6050 | 90 | 35 | C | 35 | C | 90 | 90 | — | 95 | 95 | 95 | C | 90 | 95 | C |
|   | 1.1210 | 85 | 20 | C | 0 | 95 | 90 | 90 | — | 90 | 99 | 55 | 95 | 60 | 90 | 95 |
|   | 0.2803 | 60 | 0 | 90 | 0 | 90 | 30 | 80 | — | 65 | 75 | 10 | 35 | 15 | 60 | 75 |
|   | 0.0701 | 0 | 5 | 15 | 0 | 15 | 20 | 20 | — | 0 | 0 | 5 | 0 | 10 | 0 | 0 |
|   | 0.0175 | 0 | 5 | 10 | 0 | 15 | 15 | 0 | — | 0 | 0 | 0 | 0 | 0 | 0 | 0 |
|   | 0.0087 | 0 | 0 | 0 | 0 | 0 | 0 | 0 | — | 0 | 0 | 0 | 0 | 0 | 0 | 0 |
| 5 | 5.6050 | 90 | 0 | — | 10 | — | 75 | — | — | 85 | — | 90 | — | 60 | — | — |
|   | 5.6050 | — | — | 95 | — | 98 | — | — | — | — | C | — | — | — | 98 | — |
|   | 1.1210 | 60 | 0 | — | 10 | — | 60 | — | — | 50 | — | 50 | — | 0 | — | — |
|   | 1.1210 | — | — | 95 | — | 95 | — | — | — | — | 95 | — | — | — | 95 | — |
|   | 0.2803 | — | — | 60 | — | 50 | — | — | — | — | 60 | — | — | — | 60 | — |
|   | 0.2803 | 60 | N | — | 0 | — | 50 | — | — | 30 | — | 30 | — | 0 | — | — |
|   | 0.0701 | 60 | N | — | N | — | 50 | — | — | 0 | — | 0 | — | 0 | — | — |

TABLE B-continued

Herbicide Secondary Pre, spectrums 26, 88, 91, 93, 95, 96, and 100
(C = 100% control)

|   | Rate | | | | | | | | | | | | | | | |
|---|------|---|---|---|---|---|---|---|---|---|---|---|---|---|---|---|
|   | 0.0701 | — | — | 40 | — | 10 | — | — | — | — | 20 | — | — | — | 30 | — |
| 6 | 5.6050 | 65 | 30 | 95 | 60 | 95 | 85 | 90 | — | 95 | 90 | 90 | 95 | 75 | 90 | C |
|   | 1.1210 | 80 | 0 | 90 | 15 | 95 | 95 | 85 | — | 85 | 60 | 75 | 90 | 75 | 90 | C |
|   | 1.1210 | 20 | 50 | 90 | 10 | 95 | 35 | 90 | — | 95 | 90 | 90 | 90 | 90 | 90 | 99 |
|   | 0.2803 | 30 | 15 | 85 | 0 | 90 | 80 | 80 | — | 95 | 35 | 90 | 90 | 50 | 90 | C |
|   | 0.2803 | 30 | 45 | 75 | 0 | 80 | 25 | 70 | — | 70 | 45 | 90 | 80 | 50 | 35 | 85 |
|   | 0.0701 | 10 | 15 | 70 | 0 | 50 | 0 | 55 | — | 45 | 30 | 45 | 70 | 30 | 0 | 70 |
|   | 0.0701 | 35 | 0 | 70 | 0 | 85 | 30 | 30 | — | 20 | 25 | 25 | 85 | 70 | 55 | 90 |
|   | 0.0175 | 15 | 10 | 0 | 0 | 0 | 0 | 25 | — | 10 | N | 0 | 75 | N | 0 | 40 |
|   | 0.0087 | 10 | 10 | 0 | 0 | 0 | 0 | 0 | — | 0 | 35 | 0 | 65 | 25 | 0 | 0 |
| 7 | 5.6050 | 30 | 25 | — | 0 | — | 95 | — | — | C | — | 99 | — | 75 | — | — |
|   | 5.6050 | — | — | C | — | 99 | — | — | — | — | C | — | — | — | 75 | — |
|   | 1.1210 | 50 | 20 | — | 50 | — | 98 | — | — | 99 | — | C | — | 90 | — | — |
|   | 1.1210 | — | — | C | — | 98 | — | — | — | — | 98 | — | — | — | 75 | — |
|   | 0.2803 | 70 | 0 | — | 25 | — | 80 | — | — | 98 | — | 99 | — | 80 | — | — |
|   | 0.2803 | — | — | C | — | 75 | — | — | — | — | 70 | — | — | — | 70 | — |
|   | 0.0701 | — | — | 30 | — | 65 | — | — | — | — | 40 | — | — | — | 20 | — |
|   | 0.0701 | 0 | 0 | — | 0 | — | 50 | — | — | 60 | — | 50 | — | 10 | — | — |
|   | 0.0175 | 0 | 0 | — | 0 | — | 0 | — | — | 0 | — | 0 | — | 10 | — | — |
|   | 0.0175 | — | — | 10 | — | 0 | — | — | — | — | 0 | — | — | — | 0 | — |
| 8 | 5.6050 | 95 | 50 | — | 25 | — | 95 | — | — | C | — | 98 | — | 98 | — | — |
|   | 5.6050 | — | — | 95 | — | C | — | — | — | — | 98 | — | — | — | 65 | — |
|   | 1.1210 | 40 | 5 | — | 0 | — | 0 | — | — | 95 | — | 70 | — | 40 | — | — |
|   | 1.1210 | — | — | 90 | — | C | — | — | — | — | 75 | — | — | — | 75 | — |
|   | 0.2803 | — | — | 80 | — | 98 | — | — | — | — | 20 | — | — | — | 15 | — |
|   | 0.2803 | 0 | 0 | — | 0 | — | 0 | — | — | 60 | — | 10 | — | 10 | — | — |
|   | 0.0701 | 0 | 0 | — | 0 | — | 0 | — | — | N | — | 5 | — | 10 | — | — |
|   | 0.0701 | — | — | 55 | — | N | — | — | — | — | 0 | — | — | — | 10 | — |
|   | 0.0175 | — | — | 0 | — | 50 | — | — | — | — | 0 | — | — | — | 0 | — |
|   | 0.0175 | 0 | 0 | — | 0 | — | 0 | — | — | 0 | — | 0 | — | 0 | — | — |
| 9 | 5.6050 | 75 | 40 | — | N | — | 75 | — | — | 98 | — | 99 | — | 65 | — | — |
|   | 5.6050 | — | — | 99 | — | 99 | — | — | — | — | 90 | — | — | — | 90 | — |
|   | 1.1210 | — | — | 98 | — | 95 | — | — | — | — | 90 | — | — | — | 80 | — |
|   | 1.1210 | 25 | 5 | — | N | — | 35 | — | — | 50 | — | 50 | — | 20 | — | — |
|   | 0.2803 | 10 | 5 | — | N | — | 0 | — | — | 30 | — | 25 | — | 0 | — | — |
|   | 0.2803 | — | — | 35 | — | 75 | — | — | — | — | 10 | — | — | — | 15 | — |
|   | 0.0701 | 25 | 0 | — | N | — | 0 | — | — | 20 | — | 20 | — | 0 | — | — |
|   | 0.0701 | — | — | 20 | — | 10 | — | — | — | — | 0 | — | — | — | 0 | — |
| 12 | 5.6050 | 50 | 5 | — | 0 | — | 10 | — | — | 98 | — | 95 | — | 75 | — | — |
|   | 5.6050 | — | — | 99 | — | C | — | — | — | — | 98 | — | — | — | 95 | — |
|   | 1.1210 | — | — | 95 | — | C | — | — | — | — | 98 | — | — | — | 55 | — |
|   | 1.1210 | 30 | 0 | — | 0 | — | 0 | — | — | 70 | — | 40 | — | 25 | — | — |
|   | 0.2803 | 0 | 0 | — | 0 | — | 0 | — | — | 30 | — | 25 | — | 25 | — | — |
|   | 0.2803 | — | — | 75 | — | 90 | — | — | — | — | 30 | — | — | — | 30 | — |
|   | 0.0701 | 0 | 0 | — | 0 | — | 0 | — | — | 30 | — | 40 | — | 10 | — | — |
|   | 0.0701 | — | — | 20 | — | 20 | — | — | — | — | 15 | — | — | — | 0 | — |
| 13 | 5.6050 | 70 | 25 | 70 | 0 | C | 75 | 70 | — | 80 | C | 65 | 98 | 40 | C | 95 |
|   | 1.1210 | 25 | 30 | 90 | 0 | 90 | 45 | 35 | — | 40 | 90 | 35 | 90 | 35 | 90 | 90 |
|   | 0.2803 | 45 | 15 | 30 | 0 | 40 | 0 | 0 | — | 0 | 30 | 30 | 55 | 0 | 20 | 35 |
|   | 0.0701 | 0 | 0 | 0 | 0 | N | 0 | 0 | — | 0 | 0 | N | 40 | 0 | 0 | 0 |
| 14 | 5.6050 | 80 | 40 | 95 | 5 | C | 90 | 95 | — | 90 | 95 | 95 | C | 95 | 95 | C |
|   | 1.1210 | 50 | 10 | C | 0 | 90 | 70 | 65 | — | 60 | 90 | 75 | 95 | 30 | 90 | 95 |
|   | 0.2803 | 25 | 10 | 60 | 0 | 20 | 0 | 0 | — | 0 | 55 | 35 | 85 | 10 | 80 | 60 |
|   | 0.0701 | 25 | 0 | 0 | 0 | 0 | 0 | 0 | — | 0 | 20 | 30 | 0 | 5 | 0 | 0 |
|   | 0.0175 | 0 | 0 | 0 | 0 | 0 | 0 | 0 | — | 0 | 0 | 0 | 0 | 0 | 0 | 0 |
|   | 0.0087 | 0 | 0 | 0 | 0 | 0 | 0 | 0 | — | 0 | 0 | 0 | 0 | 0 | 0 | 0 |
| 15 | 5.6050 | 85 | 0 | 90 | 0 | 95 | 80 | 70 | — | 85 | C | 45 | 95 | 95 | 95 | C |
|   | 1.1210 | 0 | 0 | 40 | 0 | 50 | 20 | 0 | — | 20 | 85 | 40 | 80 | 0 | 85 | 90 |
|   | 0.2803 | 15 | 10 | 20 | 0 | 30 | 0 | 0 | — | 0 | 50 | 25 | 85 | 20 | 75 | 75 |
|   | 0.0701 | 5 | 0 | 0 | 0 | 30 | 0 | 0 | — | 0 | 15 | 0 | 70 | 20 | 30 | 0 |
| 16 | 5.6050 | 70 | 30 | 95 | 10 | C | 70 | 75 | — | 90 | 90 | 90 | C | 95 | 95 | C |
|   | 1.1210 | 10 | 0 | 90 | 0 | 60 | 70 | 70 | — | 70 | 75 | 25 | 70 | 45 | 90 | 95 |
|   | 0.2803 | N | 0 | 0 | 30 | 20 | 0 | 0 | — | 0 | 50 | 0 | 0 | 0 | 70 | 65 |
|   | 0.0701 | 0 | 0 | 0 | 0 | 0 | 0 | 0 | — | 0 | 0 | 0 | 0 | 0 | 0 | 0 |
|   | 0.0175 | 0 | 0 | 0 | 0 | 0 | 0 | 0 | — | 0 | 0 | 0 | 0 | 0 | 0 | 0 |
| 17 | 5.6050 | 95 | 90 | C | 45 | C | C | 95 | C | C | C | C | C | C | C | C |
|   | 1.1210 | 90 | 60 | C | 30 | C | 95 | 85. | 95 | 85 | 90 | 80 | C | 85 | C | C |
|   | 0.2803 | 80 | 10 | 95 | 20 | 65 | 90 | 85 | 75 | 90 | 65 | 80 | 99 | 85 | 98 | C |
|   | 0.0701 | 25 | 0 | 55 | 0 | 35 | 45 | 45 | 75 | 30 | 25 | 30 | 65 | 20 | 30 | 90 |
|   | 0.0175 | 10 | 0 | 0 | 0 | 0 | 0 | 0 | 0 | 0 | 0 | 0 | 10 | 0 | 0 | 30 |
|   | 0.0087 | 0 | 0 | 0 | 0 | 0 | 0 | 0 | 0 | 0 | 0 | 30 | 0 | 0 | 0 | 0 |
| 18 | 5.6050 | 90 | 70 | 90 | 0 | 90 | 90 | 90 | — | 90 | C | C | C | 95 | C | C |
|   | 1.1210 | 85 | 10 | 90 | 0 | 70 | 90 | 65 | — | 80 | 45 | 60 | 95 | 70 | 90 | C |
|   | 0.2803 | 30 | 0 | 40 | 0 | 0 | 20 | 25 | — | 35 | 90 | 65 | 90 | 70 | 80 | C |
|   | 0.0701 | 0 | 0 | 0 | 0 | 0 | 0 | 0 | — | 0 | 15 | 0 | 10 | 0 | 0 | 0 |
|   | 0.0175 | 25 | 0 | 20 | 30 | 0 | N | 0 | — | 0 | 0 | 30 | 0 | 20 | 0 | 0 |
| 19 | 5.6050 | 85 | 10 | 95 | 0 | 95 | 80 | 75 | — | 85 | C | 65 | C | 95 | C | C |
|   | 1.1210 | 60 | 10 | 95 | 0 | 90 | 60 | 55 | — | 65 | 95 | 55 | 95 | 55 | 95 | C |
|   | 0.2803 | 35 | 5 | 75 | 0 | 10 | 35 | 15 | — | 55 | 95 | 20 | 50 | 20 | 60 | 95 |
|   | 0.0701 | 30 | N | N | 0 | 0 | 40 | 0 | — | 15 | 0 | 0 | 0 | 20 | 0 | 15 |

TABLE B-continued

Herbicide Secondary Pre, spectrums 26, 88, 91, 93, 95, 96, and 100
(C = 100% control)

|    | rate   |    |    |    |    |    |    |    |    |    |    |    |    |    |    |    |
|----|--------|----|----|----|----|----|----|----|----|----|----|----|----|----|----|----|
|    | 0.0175 | 0  | 0  | 5  | 0  | 0  | 0  | 20 | —  | 10 | 0  | 0  | 0  | 0  | 0  | 0  |
| 20 | 5.6050 | 65 | 20 | —  | 75 | —  | 75 | —  | —  | 80 | —  | C  | —  | 75 | —  | —  |
|    | 5.6050 | —  | —  | 95 | —  | 95 | —  | —  | —  | —  | C  | —  | —  | —  | 98 | —  |
|    | 1.1210 | 5  | 0  | —  | 0  | —  | 40 | —  | —  | 50 | —  | 70 | —  | 35 | —  | —  |
|    | 1.1210 | —  | —  | 90 | —  | 90 | —  | —  | —  | —  | 80 | —  | —  | —  | 90 | —  |
|    | 0.2803 | 0  | 0  | —  | 0  | —  | 0  | —  | —  | 0  | —  | 0  | —  | 10 | —  | —  |
|    | 0.2803 | —  | —  | 50 | —  | 15 | —  | —  | —  | —  | 20 | —  | —  | —  | 70 | —  |
|    | 0.0701 | 0  | 0  | —  | 0  | —  | 0  | —  | —  | 0  | —  | 0  | —  | 0  | —  | —  |
|    | 0.0701 | —  | —  | 0  | —  | 0  | —  | —  | —  | —  | 0  | —  | —  | —  | 50 | —  |
|    | 0.0175 | —  | —  | 0  | —  | 0  | —  | —  | —  | —  | 0  | —  | —  | —  | 0  | —  |
|    | 0.0175 | 0  | 0  | —  | 0  | —  | 0  | —  | —  | 0  | —  | 0  | —  | 0  | —  | —  |
|    | 0.0044 | 0  | 0  | —  | 0  | —  | 0  | —  | —  | 0  | —  | 0  | —  | 0  | —  | —  |
|    | 0.0044 | —  | —  | 0  | —  | 0  | —  | —  | —  | —  | 0  | —  | —  | —  | 0  | —  |
| 21 | 5.6050 | —  | —  | 99 | —  | C  | —  | —  | —  | —  | C  | —  | —  | —  | C  | —  |
|    | 5.6050 | 98 | 75 | —  | 30 | —  | 98 | —  | —  | C  | —  | C  | —  | C  | —  | —  |
|    | 1.1210 | —  | —  | 95 | —  | C  | —  | —  | —  | —  | C  | —  | —  | —  | 98 | —  |
|    | 1.1210 | 90 | 60 | —  | 0  | —  | 90 | —  | —  | 99 | —  | C  | —  | C  | —  | —  |
|    | 0.2803 | 60 | 0  | —  | 0  | —  | 30 | —  | —  | 80 | —  | 75 | —  | 75 | —  | —  |
|    | 0.2803 | —  | —  | 95 | —  | C  | —  | —  | —  | —  | 95 | —  | —  | —  | 95 | —  |
|    | 0.0701 | 0  | 0  | —  | 0  | —  | 0  | —  | —  | 60 | —  | 0  | —  | 10 | —  | —  |
|    | 0.0701 | —  | —  | 90 | —  | 40 | —  | —  | —  | —  | 65 | —  | —  | —  | 60 | —  |
|    | 0.0175 | 0  | 0  | —  | 0  | —  | 0  | —  | —  | 0  | —  | 10 | —  | 10 | —  | —  |
|    | 0.0175 | —  | —  | 90 | —  | N  | —  | —  | —  | —  | 65 | —  | —  | —  | 30 | —  |
|    | 0.0044 | 0  | 0  | —  | 0  | —  | 0  | —  | —  | 0  | —  | 0  | —  | 0  | —  | —  |
|    | 0.0044 | —  | —  | 30 | —  | 0  | —  | —  | —  | —  | 15 | —  | —  | —  | 0  | —  |
| 23 | 5.6050 | 75 | 90 | —  | 60 | —  | 95 | —  | —  | 98 | —  | 99 | —  | 95 | —  | —  |
|    | 5.6050 | —  | —  | C  | —  | 99 | —  | —  | —  | —  | 99 | —  | —  | —  | 85 | —  |
|    | 1.1210 | 60 | 60 | —  | 30 | —  | 75 | —  | —  | 99 | —  | 99 | —  | 75 | —  | —  |
|    | 1.1210 | —  | —  | 98 | —  | C  | —  | —  | —  | —  | 65 | —  | —  | —  | 70 | —  |
|    | 0.2803 | 10 | 25 | —  | 0  | —  | 30 | —  | —  | 95 | —  | 60 | —  | 40 | —  | —  |
|    | 0.2803 | —  | —  | 95 | —  | 80 | —  | —  | —  | —  | 60 | —  | —  | —  | 60 | —  |
|    | 0.0701 | —  | —  | 80 | —  | 70 | —  | —  | —  | —  | 0  | —  | —  | —  | 40 | —  |
|    | 0.0701 | 5  | 0  | —  | 0  | —  | 0  | —  | —  | 40 | —  | 25 | —  | 5  | —  | —  |
|    | 0.0178 | 25 | 20 | —  | 0  | —  | 35 | —  | —  | 35 | —  | 25 | —  | 5  | —  | —  |
|    | 0.0178 | —  | —  | 65 | —  | 60 | —  | —  | —  | —  | 0  | —  | —  | —  | 0  | —  |
| 24 | 5.6050 | 80 | 60 | —  | 40 | —  | 95 | —  | —  | 99 | —  | 40 | —  | 95 | —  | —  |
|    | 5.6050 | —  | —  | 98 | —  | C  | —  | —  | —  | —  | 80 | —  | —  | —  | 90 | —  |
|    | 1.1210 | —  | —  | 95 | —  | 60 | —  | —  | —  | —  | 60 | —  | —  | —  | 50 | —  |
|    | 1.1210 | 10 | 20 | —  | 25 | —  | 60 | —  | —  | 80 | —  | 10 | —  | 25 | —  | —  |
|    | 0.2803 | 10 | 40 | —  | 25 | —  | 30 | —  | —  | 75 | —  | 25 | —  | 20 | —  | —  |
|    | 0.2803 | —  | —  | 80 | —  | 55 | —  | —  | —  | —  | 25 | —  | —  | —  | 30 | —  |
|    | 0.0701 | 0  | 0  | —  | 0  | —  | 0  | —  | —  | 25 | —  | 0  | —  | 0  | —  | —  |
|    | 0.0701 | —  | —  | 35 | —  | N  | —  | —  | —  | —  | 25 | —  | —  | —  | 50 | —  |
|    | 0.0175 | —  | —  | 0  | —  | 0  | —  | —  | —  | —  | 0  | —  | —  | —  | 0  | —  |
|    | 0.0175 | 0  | 0  | —  | 0  | —  | 0  | —  | —  | 0  | —  | 0  | —  | 5  | —  | —  |
|    | 0.0044 | 0  | 0  | —  | 0  | —  | 0  | —  | —  | 25 | —  | 0  | —  | 0  | —  | —  |
|    | 0.0044 | —  | —  | 0  | —  | 0  | —  | —  | —  | —  | 0  | —  | —  | —  | 0  | —  |
| 25 | 5.6050 | —  | —  | 60 | —  | 90 | —  | —  | —  | —  | 60 | —  | —  | —  | 40 | —  |
|    | 5.6050 | 60 | 0  | —  | 0  | —  | 40 | —  | —  | 80 | —  | 30 | —  | 50 | —  | —  |
|    | 1.1210 | 0  | 0  | —  | 0  | —  | 0  | —  | —  | 0  | —  | 10 | —  | 0  | —  | —  |
|    | 1.1210 | —  | —  | 0  | —  | 10 | —  | —  | —  | —  | 0  | —  | —  | —  | 0  | —  |
|    | 0.2803 | 0  | 0  | —  | 0  | —  | 0  | —  | —  | 0  | —  | 10 | —  | 5  | —  | —  |
|    | 0.2803 | —  | —  | 0  | —  | 0  | —  | —  | —  | —  | 0  | —  | —  | —  | 0  | —  |
|    | 0.0701 | —  | —  | 0  | —  | 0  | —  | —  | —  | —  | 0  | —  | —  | —  | 0  | —  |
|    | 0.0701 | 0  | 0  | —  | 0  | —  | 0  | —  | —  | 0  | —  | 20 | —  | 0  | —  | —  |
| 26 | 5.6050 | —  | —  | C  | —  | C  | —  | —  | —  | —  | C  | —  | —  | —  | 98 | —  |
|    | 5.6050 | 80 | 70 | —  | 25 | —  | 95 | —  | —  | 99 | —  | 95 | —  | 98 | —  | —  |
|    | 1.1210 | —  | —  | 99 | —  | 90 | —  | —  | —  | —  | 70 | —  | —  | —  | 90 | —  |
|    | 1.1210 | 25 | 30 | —  | 25 | —  | 80 | —  | —  | 95 | —  | 70 | —  | 35 | —  | —  |
|    | 0.2803 | 0  | 0  | —  | 0  | —  | 50 | —  | —  | 60 | —  | 20 | —  | 35 | —  | —  |
|    | 0.2803 | —  | —  | 99 | —  | 90 | —  | —  | —  | —  | 50 | —  | —  | —  | 60 | —  |
|    | 0.0701 | —  | —  | 98 | —  | N  | —  | —  | —  | —  | 50 | —  | —  | —  | 50 | —  |
|    | 0.0701 | 0  | 0  | —  | 0  | —  | 0  | —  | —  | 10 | —  | 10 | —  | 5  | —  | —  |
|    | 0.0175 | —  | —  | 25 | —  | 25 | —  | —  | —  | —  | 0  | —  | —  | —  | 0  | —  |
|    | 0.0175 | 0  | 0  | —  | 0  | —  | 0  | —  | —  | 0  | —  | 0  | —  | 30 | —  | —  |
| 27 | 5.6050 | —  | —  | 99 | —  | 50 | —  | —  | —  | —  | 70 | —  | —  | —  | 40 | —  |
|    | 5.6050 | 10 | 20 | —  | 0  | —  | 50 | —  | —  | 95 | —  | 70 | —  | 35 | —  | —  |
|    | 1.1210 | 5  | 0  | —  | 20 | —  | 10 | —  | —  | 25 | —  | 30 | —  | 20 | —  | —  |
|    | 1.1210 | —  | —  | 99 | —  | N  | —  | —  | —  | —  | 50 | —  | —  | —  | 75 | —  |
|    | 0.2803 | 0  | 20 | —  | 0  | —  | 25 | —  | —  | 20 | —  | 0  | —  | 10 | —  | —  |
|    | 0.2803 | —  | —  | 75 | —  | 50 | —  | —  | —  | —  | 20 | —  | —  | —  | 25 | —  |
|    | 0.0701 | 0  | 0  | —  | 0  | —  | 0  | —  | —  | 0  | —  | 0  | —  | 0  | —  | —  |
|    | 0.0701 | —  | —  | 25 | —  | 0  | —  | —  | —  | —  | 0  | —  | —  | —  | 0  | —  |
| 29 | 5.6050 | 50 | 60 | —  | 60 | —  | 95 | —  | —  | 95 | —  | 99 | —  | 75 | —  | —  |
|    | 5.6050 | —  | —  | C  | —  | 50 | —  | —  | —  | —  | 75 | —  | —  | —  | 50 | —  |
|    | 1.1210 | 25 | 25 | —  | 25 | —  | 60 | —  | —  | 60 | —  | 30 | —  | 25 | —  | —  |
|    | 1.1210 | —  | —  | 99 | —  | 25 | —  | —  | —  | —  | 30 | —  | —  | —  | 50 | —  |
|    | 0.2803 | 0  | 10 | —  | 20 | —  | 0  | —  | —  | 30 | —  | 0  | —  | 25 | —  | —  |
|    | 0.2803 | —  | —  | 95 | —  | 25 | —  | —  | —  | —  | 10 | —  | —  | —  | 35 | —  |
|    | 0.0701 | 0  | 0  | —  | 0  | —  | 0  | —  | —  | 0  | —  | 0  | —  | 0  | —  | —  |

TABLE B-continued

Herbicide Secondary Pre, spectrums 26, 88, 91, 93, 95, 96, and 100
(C = 100% control)

| | | | | | | | | | | | | | | | | | |
|---|---|---|---|---|---|---|---|---|---|---|---|---|---|---|---|---|---|
| | 0.0701 | — | — | 75 | — | N | — | — | — | — | 0 | — | — | — | 20 | — |
| | 0.0175 | — | — | 20 | — | 0 | — | — | — | — | 0 | — | — | — | 0 | — |
| | 0.0175 | 0 | 0 | — | 0 | — | 0 | — | — | 0 | — | 0 | — | N | — | — |
| 31 | 5.6050 | 95 | 80 | — | 30 | — | 80 | — | — | 99 | — | 25 | — | 20 | — | — |
| | 5.6050 | — | — | 95 | — | 90 | — | — | — | — | 80 | — | — | — | 90 | — |
| | 1.1210 | 30 | 40 | — | 25 | — | 50 | — | — | 80 | — | 25 | — | 20 | — | — |
| | 1.1210 | — | — | 95 | — | 90 | — | — | — | — | 75 | — | — | — | 70 | — |
| | 0.2803 | — | — | 90 | — | 60 | — | — | — | — | 15 | — | — | — | 50 | — |
| | 0.2803 | 0 | 0 | — | 0 | — | 0 | — | — | 75 | — | 20 | — | 10 | — | — |
| | 0.0701 | 0 | 0 | — | 0 | — | 20 | — | — | 35 | — | 0 | — | 5 | — | — |
| | 0.0701 | — | — | 40 | — | 25 | — | — | — | — | 0 | — | — | — | 0 | — |
| | 0.0175 | 0 | 0 | — | 0 | — | 0 | — | — | 0 | — | 0 | — | 0 | — | — |
| | 0.0175 | — | — | 0 | — | 40 | — | — | — | — | 0 | — | — | — | 0 | — |
| | 0.0044 | 0 | 0 | — | 0 | — | 0 | — | — | 0 | — | 0 | — | 0 | — | — |
| | 0.0044 | — | — | 0 | — | 0 | — | — | — | — | 0 | — | — | — | 0 | — |
| 32 | 5.6050 | — | — | C | — | C | — | — | — | — | C | — | — | — | 99 | — |
| | 5.6050 | C | 75 | — | 70 | — | C | — | — | C | — | C | — | C | — | — |
| | 1.1210 | — | — | 98 | — | 70 | — | — | — | — | 80 | — | — | — | 80 | — |
| | 1.1210 | 70 | 25 | — | 25 | — | 75 | — | — | 99 | — | 80 | — | 99 | — | — |
| | 0.2803 | 60 | 20 | — | 30 | — | 60 | — | — | 95 | — | 35 | — | 75 | — | — |
| | 0.2803 | — | — | 95 | — | 60 | — | — | — | — | 40 | — | — | — | 80 | — |
| | 0.0701 | 10 | 10 | — | 0 | — | 60 | — | — | 90 | — | 30 | — | 40 | — | — |
| | 0.0701 | — | — | 30 | — | 40 | — | — | — | — | 20 | — | — | — | 30 | — |
| | 0.0175 | — | — | 0 | — | 0 | — | — | — | — | 0 | — | — | — | 0 | — |
| | 0.0175 | 0 | 10 | — | 0 | — | 0 | — | — | 0 | — | 0 | — | 5 | — | — |
| | 0.0044 | — | — | 0 | — | 0 | — | — | — | — | 0 | — | — | — | 0 | — |
| | 0.0044 | 0 | 0 | — | 0 | — | 0 | — | — | 0 | — | N | — | 0 | — | — |
| 33 | 5.6050 | — | — | C | — | 98 | — | — | — | — | C | — | — | — | 98 | — |
| | 5.6050 | 99 | 95 | — | 80 | — | C | — | — | C | — | C | — | C | — | — |
| | 1.1210 | — | — | C | — | 90 | — | — | — | — | 90 | — | — | — | 95 | — |
| | 1.1210 | 95 | 60 | — | 30 | — | 99 | — | — | 9 | — | 99 | — | 98 | — | — |
| | 0.2803 | 75 | 30 | — | 10 | — | 60 | — | — | 98 | — | 80 | — | 70 | — | — |
| | 0.2803 | — | — | C | — | 90 | — | — | — | — | 95 | — | — | — | 75 | — |
| | 0.0701 | 60 | 0 | — | 25 | — | 50 | — | — | 99 | — | 60 | — | 60* | — | — |
| | 0.0701 | — | — | 90 | — | 35 | — | — | — | — | 60 | — | — | — | 20 | — |
| | 0.0175 | — | — | 20 | — | 50 | — | — | — | — | 10 | — | — | — | 15 | — |
| | 0.0175 | 0 | 0 | — | 0 | — | 0 | — | — | 25 | — | 25 | — | 20 | — | — |
| | 0.0044 | — | — | 0 | — | 10 | — | — | — | — | 0 | — | — | — | 0 | — |
| | 0.0044 | 0 | 0 | — | 0 | — | 0 | — | — | 0 | — | 20 | — | 5 | — | — |
| 34 | 5.6050 | 50 | 40 | — | 10 | — | 75 | — | — | 98 | — | 70 | — | 50 | — | — |
| | 5.6050 | — | — | 95 | — | C | — | — | — | — | 80 | — | — | — | 80 | — |
| | 1.1210 | — | — | 90 | — | 80 | — | — | — | — | 20 | — | — | — | 40 | — |
| | 1.1210 | 10 | 0 | — | N | — | 30 | — | — | 60 | — | 30 | — | 20 | — | — |
| | 0.2803 | 0 | 0 | — | 0 | — | 0 | — | — | 0 | — | 10 | — | 0 | — | — |
| | 0.2803 | — | — | 40 | — | 70 | — | — | — | — | 10 | — | — | — | 40 | — |
| | 0.0701 | 0 | 0 | — | 0 | — | 0 | — | — | 0 | — | 0 | — | 0 | — | — |
| | 0.0701 | — | — | 0 | — | 50 | — | — | — | — | 0 | — | — | — | 30 | — |
| 35 | 5.6050 | — | — | 99 | — | 95 | — | — | — | — | 90 | — | — | — | 80 | — |
| | 5.6050 | 70 | 65 | — | 20 | — | 99 | — | — | 95 | — | 99 | — | 95 | — | — |
| | 1.1210 | — | — | 65 | — | 10 | — | — | — | — | 50 | — | — | — | 50 | — |
| | 1.1210 | 0 | 0 | — | 0 | — | 90 | — | — | 70 | — | 40 | — | 0 | — | — |
| | 0.2803 | 0 | 0 | — | 0 | — | 0 | — | — | 0 | — | 0 | — | 0 | — | — |
| | 0.2803 | — | — | 10 | — | 0 | — | — | — | — | 10 | — | — | — | 20 | — |
| | 0.0701 | 0 | 0 | — | 0 | — | 0 | — | — | 0 | — | 0 | — | 0 | — | — |
| | 0.0701 | — | — | 0 | — | 0 | — | — | — | — | 0 | — | — | — | 0 | — |
| 36 | 11.2100 | — | — | 55 | — | 70 | — | — | — | — | 10 | — | — | — | 0 | — |
| | 11.2100 | 0 | 0 | — | 0 | — | 40 | — | — | 30 | — | 0 | — | 0 | — | — |
| | 5.6050 | 0 | 0 | — | 0 | — | 0 | — | — | 0 | — | 0 | — | 0 | — | — |
| | 5.6050 | — | — | 10 | — | 0 | — | — | — | — | 0 | — | — | — | 0 | — |
| | 1.1210 | 0 | 0 | — | 0 | — | 30 | — | — | 0 | — | 0 | — | 0 | — | — |
| | 1.1210 | — | — | 0 | — | 0 | — | — | — | — | 0 | — | — | — | 0 | — |
| 37 | 11.2100 | — | — | 90 | — | 30 | — | — | — | — | 10 | — | — | — | 20 | — |
| | 11.2100 | 25 | 0 | — | 0 | — | 95 | — | — | 80 | — | 99 | — | 70 | — | — |
| | 5.6050 | 10 | 0 | — | 0 | — | 75 | — | — | 65 | — | 10 | — | 25 | — | — |
| | 5.6050 | — | — | 90 | — | 55 | — | — | — | — | 0 | — | — | — | 50 | — |
| | 1.1210 | 0 | 0 | — | 0 | — | 0 | — | — | 0 | — | 0 | — | 0 | — | — |
| | 1.1210 | — | — | 10 | — | 50 | — | — | — | — | 0 | — | — | — | 0 | — |
| 38 | 5.6050 | 95 | 98 | — | 70 | — | 99 | — | — | 99 | — | 99 | — | 99 | — | — |
| | 5.6050 | — | — | C | — | C | — | — | — | — | C | — | — | — | C | — |
| | 1.1210 | — | — | 95 | — | 99 | — | — | — | — | 99 | — | — | — | 75 | — |
| | 1.1210 | 75 | 75 | — | 60 | — | 95 | — | — | 98 | — | 70 | — | 98 | — | — |
| | 0.2803 | 65 | 40 | — | 5 | — | 99 | — | — | 95 | — | 75 | — | 75 | — | — |
| | 0.2803 | — | — | 20 | — | C | — | — | — | — | 55 | — | — | — | 65 | — |
| | 0.0701 | 0 | 75 | — | 0 | — | 20 | — | — | 20 | — | 20 | — | 10 | — | — |
| | 0.0701 | — | — | 15 | — | 75 | — | — | — | — | 45 | — | — | — | 45 | — |
| | 0.0175 | 0 | 40 | — | 0 | — | 20 | — | — | 0 | — | 30 | — | 0 | — | — |
| | 0.0175 | — | — | 0 | — | 70 | — | — | — | — | 15 | — | — | — | 20 | — |
| | 0.0044 | 0 | 0 | — | 0 | — | 0 | — | — | 0 | — | 5 | — | 0 | — | — |
| | 0.0044 | — | — | 0 | — | 5 | — | — | — | — | 0 | — | — | — | 0 | — |
| 39 | 5.6050 | 95 | 15 | 95 | 45 | 95 | 85 | 85 | 70 | 85 | 95 | 95 | 95 | 85 | 95 | C |

TABLE B-continued

Herbicide Secondary Pre, spectrums 26, 88, 91, 93, 95, 96, and 100
(C = 100% control)

| | | | | | | | | | | | | | | | |
|---|---|---|---|---|---|---|---|---|---|---|---|---|---|---|---|
| 1.1210 | 45 | 30 | 90 | N | 80 | 55 | 55 | 70 | 90 | 90 | 55 | 70 | 30 | 90 | C |
| 0.2803 | 0 | 15 | 80 | N | 70 | 35 | 55 | 70 | 50 | 70 | 50 | 50 | 30 | 85 | 95 |
| 0.0701 | 20 | 10 | 0 | 0 | 35 | 0 | 0 | 25 | 0 | 0 | 20 | 0 | 0 | 35 | 30 |
| 0.0175 | N | 0 | N | 0 | 0 | 0 | 0 | 0 | 0 | 0 | 0 | 0 | 20 | 25 | 0 |
| 0.0087 | 0 | 0 | 0 | 0 | 0 | 0 | 0 | 0 | 0 | 0 | N | 0 | 0 | 0 | 0 |

| Ex. No. | Rate kg/ha | Bygr | Lacg | Grft | Sube | Colq | Pesw | Cocw | Anbg | Barz | Ruth | Sejg | Wioa | Cwbs | Blgr |
|---|---|---|---|---|---|---|---|---|---|---|---|---|---|---|---|
| 1 | 5.6050 | C | C | C | — | — | — | — | — | — | — | — | — | — | — |
| | 1.1210 | C | C | C | — | — | — | — | — | — | — | — | — | — | — |
| | 0.2803 | C | C | C | — | — | — | — | — | — | — | — | — | — | — |
| | 0.0701 | 90 | 85 | 90 | — | — | — | — | — | — | — | — | — | — | — |
| | 0.0175 | 0 | 0 | 40 | — | — | — | — | — | — | — | — | — | — | — |
| | 0.0087 | 5 | 0 | 0 | — | — | — | — | — | — | — | — | — | — | — |
| 2 | 5.6050 | C | C | C | — | — | — | C | — | — | — | — | — | — | — |
| | 1.1210 | C | C | C | — | — | — | C | — | — | — | — | — | — | — |
| | 0.2803 | C | C | C | — | — | — | C | — | — | — | — | — | — | — |
| | 0.0701 | C | C | C | — | — | — | C | — | — | — | — | — | — | — |
| | 0.0175 | 95 | C | C | — | — | — | 90 | — | — | — | — | — | — | — |
| | 0.0087 | 90 | 98 | 95 | — | — | — | C | — | — | — | — | — | — | — |
| 3 | 5.6050 | C | C | C | — | — | — | C | — | — | — | — | — | — | — |
| | 1.1210 | C | C | C | — | — | — | C | — | — | — | — | — | — | — |
| | 0.2803 | 95 | C | C | — | — | — | 95 | — | — | — | — | — | — | — |
| | 0.0701 | 0 | C | 15 | — | — | — | 0 | — | — | — | — | — | — | — |
| | 0.0175 | N | 95 | N | — | — | — | 0 | — | — | — | — | — | — | — |
| | 0.0087 | 0 | 85 | 30 | — | — | — | 0 | — | — | — | — | — | — | — |
| 4 | 5.6050 | C | C | C | — | — | — | C | — | — | — | — | — | — | — |
| | 1.1210 | C | C | C | — | — | — | 95 | — | — | — | — | — | — | — |
| | 0.2803 | 95 | C | 95 | — | — | — | 95 | — | — | — | — | — | — | — |
| | 0.0701 | 0 | 95 | 30 | — | — | — | 10 | — | — | — | — | — | — | — |
| | 0.0175 | 0 | 809 | 0 | — | — | — | 15 | — | — | — | — | — | — | — |
| | 0.0087 | 0 | 30 | 0 | — | — | — | 0 | — | — | — | — | — | — | — |
| 5 | 5.6050 | C | C | — | — | — | — | — | — | — | — | — | 95 | — | — |
| | 5.6050 | — | — | C | — | — | — | C | C | 70 | 60 | — | 98 | — | — |
| | 1.1210 | C | C | — | — | — | — | — | — | — | — | 95 | — | — | — |
| | 1.1210 | — | — | C | — | — | — | C | C | 50 | 40 | — | 98 | — | — |
| | 0.2803 | — | — | 99 | — | — | — | 90 | C | 25 | 0 | — | 75 | — | — |
| | 0.2803 | 98 | C | — | — | — | — | — | — | — | — | 90 | — | — | — |
| | 0.0701 | 70 | 85 | — | — | — | — | — | — | — | — | 60 | — | — | — |
| | 0.0701 | — | — | 90 | — | — | — | 30 | 90 | 10 | 0 | — | 40 | — | — |
| 6 | 5.6050 | C | C | 95 | — | — | — | C | — | — | — | — | — | — | — |
| | 1.1210 | 95 | C | 99 | — | — | — | C | — | — | — | — | — | — | — |
| | 1.1210 | C | C | 97 | — | — | — | C | — | — | — | — | — | — | — |
| | 0.2803 | C | C | C | — | — | — | C | — | — | — | — | — | — | — |
| | 0.2803 | 97 | 90 | 95 | — | — | — | 90 | — | — | — | — | — | — | — |
| | 0.0701 | 80 | C | 80 | — | — | — | 95 | — | — | — | — | — | — | — |
| | 0.0701 | 98 | 99 | 95 | — | — | — | C | — | — | — | — | — | — | — |
| | 0.0175 | 40 | 40 | 20 | — | — | — | 0 | — | — | — | — | — | — | — |
| | 0.0087 | 0 | 95 | 30 | — | — | — | 0 | — | — | — | — | — | — | — |
| 7 | 5.6050 | C | C | — | — | — | — | — | — | — | — | C | — | — | — |
| | 5.6050 | — | — | C | — | — | — | C | C | 75 | 95 | — | 95 | — | — |
| | 1.1210 | C | C | — | — | — | — | — | — | — | — | 99 | — | — | — |
| | 1.1210 | — | — | C | — | — | — | C | C | 75 | 90 | — | 95 | — | — |
| | 0.2803 | C | C | — | — | — | — | — | — | — | — | 98 | — | — | — |
| | 0.2803 | — | — | C | — | — | — | C | C | 40 | 80 | — | 80 | — | — |
| | 0.0701 | — | — | 99 | — | — | — | 90 | C | 25 | 75 | — | 40 | — | — |
| | 0.0701 | 98 | C | — | — | — | — | — | — | — | — | 90 | — | — | — |
| | 0.0175 | 35 | 98 | — | — | — | — | — | — | — | — | 60 | — | — | — |
| | 0.0175 | — | — | 30 | — | — | — | 0 | 50 | 0 | 0 | — | 0 | — | — |
| 8 | 5.6050 | C | C | — | — | — | — | — | — | — | — | C | — | — | — |
| | 5.6050 | — | — | C | — | — | — | C | C | 35 | 90 | — | 90 | — | — |
| | 1.1210 | C | C | — | — | — | — | — | — | — | — | C | — | — | — |
| | 1.1210 | — | — | C | — | — | — | C | C | 10 | 80 | — | 60 | — | — |
| | 0.2803 | — | — | 90 | — | — | — | 85 | 99 | 0 | 50 | — | 60 | — | — |
| | 0.2803 | 99 | C | — | — | — | — | — | — | — | — | 70 | — | — | — |
| | 0.0701 | 20 | 90 | — | — | — | — | — | — | — | — | 20 | — | — | — |
| | 0.0701 | — | — | 50 | — | — | — | 75 | 90 | 0 | 10 | — | 15 | — | — |
| | 0.0175 | — | — | 0 | — | — | — | N | 50 | 0 | 20 | — | 20 | — | — |
| | 0.0175 | 0 | 80 | — | — | — | — | — | — | — | — | 0 | — | — | — |
| 9 | 5.6050 | C | C | — | — | — | — | — | — | — | — | C | — | — | — |
| | 5.6050 | — | — | C | — | — | — | C | C | 40 | 70 | — | 95 | — | — |
| | 1.1210 | — | — | C | — | — | — | C | C | 0 | 40 | — | 90 | — | — |
| | 1.1210 | C | C | — | — | — | — | — | — | — | — | 80 | — | — | — |
| | 0.2803 | 25 | 98 | — | — | — | — | — | — | — | — | 30 | — | — | — |
| | 0.2803 | — | — | 10 | — | — | — | 10 | 95 | 0 | 10 | — | 0 | — | — |
| | 0.0701 | 10 | 80 | — | — | — | — | — | — | — | — | 25 | — | — | — |
| | 0.0701 | — | — | 0 | — | — | — | 0 | 10 | 0 | 0 | — | 0 | — | — |
| 12 | 5.6050 | C | C | — | — | — | — | — | — | — | — | C | — | — | — |
| | 5.6050 | — | — | C | — | — | — | 99 | C | 35 | 65 | — | 90 | — | — |
| | 1.1210 | — | — | 95 | — | — | — | 98 | C | 10 | N | — | 75 | — | — |

TABLE B-continued

Herbicide Secondary Pre, spectrums 26, 88, 91, 93, 95, 96, and 100
(C = 100% control)

|    | Rate   |    |    |    |   |   |   |    |    |    |    |    |    |    |    |
|----|--------|----|----|----|---|---|---|----|----|----|----|----|----|----|----|
|    | 1.1210 | C  | C  | —  | — | — | — | —  | —  | —  | —  | 99 | —  | —  | —  |
|    | 0.2803 | 80 | C  | —  | — | — | — | —  | —  | —  | —  | 98 | —  | —  | —  |
|    | 0.2803 | —  | —  | 80 | — | — | — | 80 | 90 | 15 | 50 | —  | 60 | —  | —  |
|    | 0.0701 | 0  | 90 | —  | — | — | — | —  | —  | —  | —  | 40 | —  | —  | —  |
|    | 0.0701 | —  | —  | 0  | — | — | — | 10 | 65 | 0  | 50 | —  | 15 | —  | —  |
| 13 | 5.6050 | C  | C  | C  | — | — | — | C  | —  | —  | —  | —  | —  | —  | —  |
|    | 1.1210 | C  | C  | C  | — | — | — | 95 | —  | —  | —  | —  | —  | —  | —  |
|    | 0.2803 | 95 | C  | 95 | — | — | — | 90 | —  | —  | —  | —  | —  | —  | —  |
|    | 0.0701 | 0  | 95 | 30 | — | — | — | 80 | —  | —  | —  | —  | —  | —  | —  |
| 14 | 5.6050 | C  | C  | C  | — | — | — | C  | —  | —  | —  | —  | —  | —  | —  |
|    | 1.1210 | C  | C  | C  | — | — | — | C  | —  | —  | —  | —  | —  | —  | —  |
|    | 0.2803 | 90 | 80 | 85 | — | — | — | 90 | —  | —  | —  | —  | —  | —  | —  |
|    | 0.0701 | 45 | 40 | 70 | — | — | — | 70 | —  | —  | —  | —  | —  | —  | —  |
|    | 0.0175 | 0  | 0  | 0  | — | — | — | 0  | —  | —  | —  | —  | —  | —  | —  |
|    | 0.0087 | 0  | 0  | 0  | — | — | — | 0  | —  | —  | —  | —  | —  | —  | —  |
| 15 | 5.6050 | C  | C  | C  | — | — | — | C  | —  | —  | —  | —  | —  | —  | —  |
|    | 1.1210 | 95 | C  | 95 | — | — | — | C  | —  | —  | —  | —  | —  | —  | —  |
|    | 0.2803 | 65 | 95 | 60 | — | — | — | 90 | —  | —  | —  | —  | —  | —  | —  |
|    | 0.0701 | 0  | 0  | 30 | — | — | — | 55 | —  | —  | —  | —  | —  | —  | —  |
| 16 | 5.6050 | C  | C  | C  | — | — | — | C  | —  | —  | —  | —  | —  | —  | —  |
|    | 1.1210 | C  | C  | 95 | — | — | — | C  | —  | —  | —  | —  | —  | —  | —  |
|    | 0.2803 | 75 | C  | 70 | — | — | — | 35 | —  | —  | —  | —  | —  | —  | —  |
|    | 0.0701 | 0  | 0  | 0  | — | — | — | 0  | —  | —  | —  | —  | —  | —  | —  |
|    | 0.0175 | 0  | 0  | 0  | — | — | — | 0  | —  | —  | —  | —  | —  | —  | —  |
| 17 | 5.6050 | C  | C  | C  | — | — | — | —  | —  | —  | —  | —  | —  | —  | —  |
|    | 1.1210 | C  | C  | C  | — | — | — | —  | —  | —  | —  | —  | —  | —  | —  |
|    | 0.2803 | C  | C  | 98 | — | — | — | —  | —  | —  | —  | —  | —  | —  | —  |
|    | 0.0701 | 95 | C  | 90 | — | — | — | —  | —  | —  | —  | —  | —  | —  | —  |
|    | 0.0175 | 85 | 75 | 35 | — | — | — | —  | —  | —  | —  | —  | —  | —  | —  |
|    | 0.0087 | 0  | 35 | 0  | — | — | — | —  | —  | —  | —  | —  | —  | —  | —  |
| 18 | 5.6050 | C  | C  | C  | — | — | — | C  | —  | —  | —  | —  | —  | —  | —  |
|    | 1.1210 | C  | C  | 99 | — | — | — | C  | —  | —  | —  | —  | —  | —  | —  |
|    | 0.2803 | 95 | 95 | 95 | — | — | — | 30 | —  | —  | —  | —  | —  | —  | —  |
|    | 0.0701 | 65 | 55 | 60 | — | — | — | 0  | —  | —  | —  | —  | —  | —  | —  |
|    | 0.0175 | 35 | 50 | 60 | — | — | — | 30 | —  | —  | —  | —  | —  | —  | —  |
| 19 | 5.6050 | C  | C  | C  | — | — | — | C  | —  | —  | —  | —  | —  | —  | —  |
|    | 1.1210 | C  | C  | C  | — | — | — | 90 | —  | —  | —  | —  | —  | —  | —  |
|    | 0.2803 | C  | C  | C  | — | — | — | 15 | —  | —  | —  | —  | —  | —  | —  |
|    | 0.0701 | 0  | 95 | 0  | — | — | — | 0  | —  | —  | —  | —  | —  | —  | —  |
|    | 0.0175 | 0  | 75 | 0  | — | — | — | 55 | —  | —  | —  | —  | —  | —  | —  |
| 20 | 5.6050 | C  | C  | —  | — | — | — | —  | —  | —  | —  | C  | —  | —  | —  |
|    | 5.6050 | —  | —  | C  | — | — | — | C  | C  | 40 | 70 | —  | 99 | —  | —  |
|    | 1.1210 | C  | C  | —  | — | — | — | —  | —  | —  | —  | C  | —  | —  | —  |
|    | 1.1210 | —  | —  | C  | — | — | — | 95 | C  | 20 | 30 | —  | 90 | —  | —  |
|    | 0.2803 | 99 | 99 | —  | — | — | — | —  | —  | —  | —  | 75 | —  | —  | —  |
|    | 0.2803 | —  | —  | C  | — | — | — | 75 | 99 | 0  | 0  | —  | 80 | —  | —  |
|    | 0.0701 | 0  | 75 | —  | — | — | — | —  | —  | —  | —  | 20 | —  | —  | —  |
|    | 0.0701 | —  | —  | 90 | — | — | — | 15 | 99 | 0  | 0  | —  | 25 | —  | —  |
|    | 0.0175 | —  | —  | 50 | — | — | — | 0  | 10 | 0  | 0  | —  | 0  | —  | —  |
|    | 0.0175 | 10 | 0  | —  | — | — | — | —  | —  | —  | —  | 0  | —  | —  | —  |
|    | 0.0044 | 0  | 0  | —  | — | — | — | —  | —  | —  | —  | 0  | —  | —  | —  |
|    | 0.0044 | —  | —  | 0  | — | — | — | 0  | 0  | 0  | 0  | —  | 0  | —  | —  |
| 21 | 5.6050 | —  | —  | C  | — | — | — | C  | C  | 95 | 90 | —  | C  | —  | —  |
|    | 5.6050 | C  | C  | —  | — | — | — | —  | —  | —  | —  | C  | —  | —  | —  |
|    | 1.1210 | —  | —  | C  | — | — | — | C  | C  | 50 | 60 | —  | C  | —  | —  |
|    | 1.1210 | C  | C  | —  | — | — | — | —  | —  | —  | —  | C  | —  | —  | —  |
|    | 0.2803 | C  | C  | —  | — | — | — | —  | —  | —  | —  | C  | —  | —  | —  |
|    | 0.2803 | —  | —  | C  | — | — | — | C  | C  | 45 | 50 | —  | 90 | —  | —  |
|    | 0.0701 | C  | C  | —  | — | — | — | —  | —  | —  | —  | 98 | —  | —  | —  |
|    | 0.0701 | —  | —  | 99 | — | — | — | C  | 98 | 15 | 30 | —  | 90 | —  | —  |
|    | 0.0175 | 95 | C  | —  | — | — | — | —  | —  | —  | —  | 75 | —  | —  | —  |
|    | 0.0175 | —  | —  | 98 | — | — | — | C  | C  | 0  | 40 | —  | 75 | —  | —  |
|    | 0.0044 | 0  | 80 | —  | — | — | — | —  | —  | —  | —  | 20 | —  | —  | —  |
|    | 0.0044 | —  | —  | 0  | — | — | — | 80 | 15 | 0  | 0  | —  | 0  | —  | —  |
| 23 | 5.6050 | C  | C  | —  | — | — | — | —  | —  | —  | —  | 99 | —  | —  | —  |
|    | 5.6050 | —  | —  | C  | — | — | — | C  | C  | 55 | 95 | —  | 99 | —  | —  |
|    | 1.1210 | C  | C  | —  | — | — | — | —  | —  | —  | —  | 99 | —  | —  | —  |
|    | 1.1210 | —  | —  | C  | — | — | — | C  | C  | 25 | 80 | —  | 95 | —  | —  |
|    | 0.2803 | C  | C  | —  | — | — | — | —  | —  | —  | —  | 75 | —  | —  | —  |
|    | 0.2803 | —  | —  | 99 | — | — | — | C  | C  | 25 | 60 | —  | 80 | —  | —  |
|    | 0.0701 | —  | —  | 98 | — | — | — | C  | 98 | 0  | 50 | —  | 80 | —  | —  |
|    | 0.0701 | 95 | C  | —  | — | — | — | —  | —  | —  | —  | 30 | —  | —  | —  |
|    | 0.0178 | 20 | 95 | —  | — | — | — | —  | —  | —  | —  | 25 | —  | —  | —  |
|    | 0.0178 | —  | —  | 70 | — | — | — | 80 | 80 | 0  | 50 | —  | 60 | —  | —  |
| 24 | 5.6050 | C  | C  | —  | — | — | — | —  | —  | —  | —  | C  | —  | —  | —  |
|    | 5.6050 | —  | —  | C  | — | — | — | C  | C  | 90 | C  | —  | 80 | —  | —  |
|    | 1.1210 | —  | —  | 99 | — | — | — | C  | C  | 30 | 60 | —  | 50 | —  | —  |
|    | 1.1210 | C  | C  | —  | — | — | — | —  | —  | —  | —  | 65 | —  | —  | —  |
|    | 0.2803 | C  | C  | —  | — | — | — | —  | —  | —  | —  | 90 | —  | —  | —  |
|    | 0.2803 | —  | —  | 98 | — | — | — | C  | C  | 20 | 20 | —  | 30 | —  | —  |

TABLE B-continued

Herbicide Secondary Pre, spectrums 26, 88, 91, 93, 95, 96, and 100
(C = 100% control)

| | | | | | | | | | | | | | | | |
|---|---|---|---|---|---|---|---|---|---|---|---|---|---|---|---|
| | 0.0701 | 30 | 95 | — | — | — | — | — | — | — | — | 0 | — | — | — |
| | 0.0701 | — | — | 15 | — | — | — | 50 | 98 | 20 | N | — | 35 | — | — |
| | 0.0175 | — | — | 0 | — | — | — | 0 | 0 | 0 | 0 | — | 0 | — | — |
| | 0.0175 | 25 | 30 | — | — | — | — | — | — | — | — | 0 | — | — | — |
| | 0.0044 | 0 | 0 | — | — | — | — | — | — | — | — | 0 | — | — | — |
| | 0.0044 | — | — | 0 | — | — | — | 0 | 0 | 0 | 0 | — | 0 | — | — |
| 25 | 5.6050 | — | — | 99 | — | — | — | 95 | 99 | 20 | 80 | — | 50 | — | — |
| | 5.6050 | 99 | C | — | — | — | — | — | — | — | — | 95 | — | — | — |
| | 1.1210 | 20 | 90 | — | — | — | — | — | — | — | — | 5 | — | — | — |
| | 1.1210 | — | — | 65 | — | — | — | 50 | 10 | 0 | 40 | — | 50 | — | — |
| | 0.2803 | 0 | 25 | — | — | — | — | — | — | — | — | 0 | — | — | — |
| | 0.2803 | — | — | 0 | — | — | — | 0 | 0 | 0 | 20 | — | 0 | — | — |
| | 0.0701 | — | — | 0 | — | — | — | 0 | 0 | 0 | 0 | — | 0 | — | — |
| | 0.0701 | 0 | 0 | — | — | — | — | — | — | — | — | 0 | — | — | — |
| 26 | 5.6050 | — | — | C | — | — | — | C | C | 50 | 80 | — | C | — | — |
| | 5.6050 | C | C | — | — | — | — | — | — | — | — | 98 | — | — | — |
| | 1.1210 | — | — | C | — | — | — | C | C | 20 | 80 | — | 90 | — | — |
| | 1.1210 | C | C | — | — | — | — | — | — | — | — | C | — | — | — |
| | 0.2803 | C | 99 | — | — | — | — | — | — | — | — | 95 | — | — | — |
| | 0.2803 | — | — | C | — | — | — | C | C | 10 | 25 | — | 80 | — | — |
| | 0.0701 | — | — | 80 | — | — | — | N | C | 10 | N | — | 70 | — | — |
| | 0.0701 | 75 | 99 | — | — | — | — | — | — | — | — | 50 | — | — | — |
| | 0.0175 | — | — | 0 | — | — | — | 0 | 75 | 0 | 25 | — | 0 | — | — |
| | 0.0175 | 10 | 35 | — | — | — | — | — | — | — | — | 0 | — | — | — |
| 27 | 5.6050 | — | — | C | — | — | — | C | C | 20 | 50 | — | 95 | — | — |
| | 5.6050 | C | C | — | — | — | — | — | — | — | — | 98 | — | — | — |
| | 1.1210 | 99 | C | — | — | — | — | — | — | — | — | 98 | — | — | — |
| | 1.1210 | — | — | C | — | — | — | 80 | C | 10 | N | — | 80 | — | — |
| | 0.2803 | 40 | 99 | — | — | — | — | — | — | — | — | 20 | — | — | — |
| | 0.2803 | — | — | 99 | — | — | — | 60 | C | 0 | 40 | — | 50 | — | — |
| | 0.0701 | 0 | 80 | — | — | — | — | — | — | — | — | 25 | — | — | — |
| | 0.0701 | — | — | 30 | — | — | — | 0 | 60 | 0 | 25 | — | 0 | — | — |
| 29 | 5.6050 | C | C | — | — | — | — | — | — | — | — | C | — | — | — |
| | 5.6050 | — | — | C | — | — | — | C | C | 30 | 80 | — | 80 | — | — |
| | 1.1210 | 99 | C | — | — | — | — | — | — | — | — | 95 | — | — | — |
| | 1.1210 | — | — | C | — | — | — | 35 | C | 0 | 40 | — | 75 | — | — |
| | 0.2803 | 98 | C | — | — | — | — | — | — | — | — | 95 | — | — | — |
| | 0.2803 | — | — | C | — | — | — | 25 | 98 | 0 | 25 | — | 60 | — | — |
| | 0.0701 | 20 | 80 | — | — | — | — | — | — | — | — | 0 | — | — | — |
| | 0.0701 | — | — | 80 | — | — | — | 0 | 90 | 0 | N | — | 70 | — | — |
| | 0.0175 | — | — | 0 | — | — | — | 0 | 20 | 0 | 0 | — | 0 | — | — |
| | 0.0175 | 0 | 40 | — | — | — | — | — | — | — | — | 20 | — | — | — |
| 31 | 5.6050 | C | C | — | — | — | — | — | — | — | — | C | — | — | — |
| | 5.6050 | — | — | C | — | — | — | C | C | 40 | 90 | — | 85 | — | — |
| | 1.1210 | 99 | C | — | — | — | — | — | — | — | — | 75 | — | — | — |
| | 1.1210 | — | — | 98 | — | — | — | 98 | C | 10 | 50 | — | 80 | — | — |
| | 0.2803 | — | — | 60 | — | — | — | 99 | C | 0 | 30 | — | 20 | — | — |
| | 0.2803 | 65 | C | — | — | — | — | — | — | — | — | 40 | — | — | — |
| | 0.0701 | 25 | 99 | — | — | — | — | — | — | — | — | 30 | — | — | — |
| | 0.0701 | — | — | 20 | — | — | — | 70 | 85 | 0 | 20 | — | 20 | — | — |
| | 0.0175 | 20 | 30 | — | — | — | — | — | — | — | — | 0 | — | — | — |
| | 0.0175 | — | — | 20 | — | — | — | 20 | 80 | 0 | 20 | — | 0 | — | — |
| | 0.0044 | 0 | 0 | — | — | — | — | — | — | — | — | 0 | — | — | — |
| | 0.0044 | — | — | 0 | — | — | — | 0 | 15 | 0 | 0 | — | 0 | — | — |
| 32 | 5.6050 | — | — | C | — | — | — | C | C | 95 | 95 | — | 98 | — | — |
| | 5.6050 | C | C | — | — | — | — | — | — | — | — | C | — | — | — |
| | 1.1210 | — | — | 99 | — | — | — | C | C | 75 | 65 | — | 90 | — | — |
| | 1.1210 | C | C | — | — | — | — | — | — | — | — | C | — | — | — |
| | 0.2803 | C | C | — | — | — | — | — | — | — | — | C | — | — | — |
| | 0.2803 | — | — | 95 | — | — | — | 90 | C | 25 | 10 | — | 85 | — | — |
| | 0.0701 | C | C | — | — | — | — | — | — | — | — | 95 | — | — | — |
| | 0.0701 | — | — | 70 | — | — | — | 80 | C | 0 | 10 | — | 30 | — | — |
| | 0.0175 | — | — | 30 | — | — | — | 0 | 90 | 0 | 0 | — | 0 | — | — |
| | 0.0175 | 30 | 70 | — | — | — | — | — | — | — | — | 0 | — | — | — |
| | 0.0044 | — | — | 0 | — | — | — | 0 | 15 | 0 | 0 | — | 0 | — | — |
| | 0.0044 | 0 | 25 | — | — | — | — | — | — | — | — | 0 | — | — | — |
| 33 | 5.6050 | — | — | C | — | — | — | C | C | 90 | 85 | — | C | — | — |
| | 5.6050 | C | C | — | — | — | — | — | — | — | — | C | — | — | — |
| | 1.1210 | — | — | C | — | — | — | C | C | 80 | 40 | — | 99 | — | — |
| | 1.1210 | C | C | — | — | — | — | — | — | — | — | C | — | — | — |
| | 0.2803 | C | C | — | — | — | — | — | — | — | — | C | — | — | — |
| | 0.2803 | — | — | C | — | — | — | 99 | C | 30 | 50 | — | 98 | — | — |
| | 0.0701 | C | C | — | — | — | — | — | — | — | — | C | — | — | — |
| | 0.0701 | — | — | 99 | — | — | — | 90 | 99 | 15 | 30 | — | 80 | — | — |
| | 0.0175 | — | — | 65 | — | — | — | 60 | 95 | 0 | 10 | — | 50 | — | — |
| | 0.0175 | 99 | 98 | — | — | — | — | — | — | — | — | 25 | — | — | — |
| | 0.0044 | — | — | 15 | — | — | — | 0 | 15 | 0 | 0 | — | 0 | — | — |
| | 0.0044 | 0 | 75 | — | — | — | — | — | — | — | — | 20 | — | — | — |
| 34 | 5.6050 | C | C | — | — | — | — | — | — | — | — | C | — | — | — |
| | 5.6050 | — | — | C | — | — | — | C | C | 30 | 80 | — | 90 | — | — |

TABLE B-continued

Herbicide Secondary Pre, spectrums 26, 88, 91, 93, 95, 96, and 100
(C = 100% control)

| Group | Rate | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| | 1.1210 | — | — | C | — | — | — | 90 | 99 | 25 | 30 | — | 65 | — | — |
| | 1.1210 | 98 | C | — | — | — | — | — | — | — | — | 98 | — | — | — |
| | 0.2803 | 10 | 99 | — | — | — | — | — | — | — | — | 30 | — | — | — |
| | 0.2803 | — | — | 60 | — | — | — | 70 | 90 | 10 | 20 | — | 30 | — | — |
| | 0.0701 | 0 | 60 | — | — | — | — | — | — | — | — | 0 | — | — | — |
| | 0.0701 | — | — | 0 | — | — | — | 0 | 20 | 0 | 40 | — | 0 | — | — |
| 35 | 5.6050 | — | — | C | — | — | — | C | C | 50 | 60 | — | 85 | — | — |
| | 5.6050 | C | C | — | — | — | — | — | — | — | — | C | — | — | — |
| | 1.1210 | — | — | C | — | — | — | 85 | C | 20 | 20 | — | 40 | — | — |
| | 1.1210 | C | C | — | — | — | — | — | — | — | — | 99 | — | — | — |
| | 0.2803 | 95 | 90 | — | — | — | — | — | — | — | — | 65 | — | — | — |
| | 0.2803 | — | — | 95 | — | — | — | 30 | 99 | 0 | 0 | — | 10 | — | — |
| | 0.0701 | 0 | 30 | — | — | — | — | — | — | — | — | 20 | — | — | — |
| | 0.0701 | — | — | 60 | — | — | — | 0 | 0 | 0 | 0 | — | 0 | — | — |
| 36 | 11.2100 | — | — | 90 | — | — | — | 20 | 0 | 10 | 80 | — | 15 | — | — |
| | 11.2100 | 0 | 60 | — | — | — | — | — | — | — | — | 0 | — | — | — |
| | 5.6050 | 0 | 25 | — | — | — | — | — | — | — | — | 0 | — | — | — |
| | 5.6050 | — | — | 80 | — | — | — | 0 | 0 | 0 | 0 | — | 0 | — | — |
| | 1.1210 | 0 | 25 | — | — | — | — | — | — | — | — | 0 | — | — | — |
| | 1.1210 | — | — | 90 | — | — | — | 0 | 0 | 0 | 0 | — | 0 | — | — |
| 37 | 11.2100 | — | — | C | — | — | — | 95 | 95 | 10 | 20 | — | 60 | — | — |
| | 11.2100 | C | C | — | — | — | — | — | — | — | — | C | — | — | — |
| | 5.6050 | 99 | C | — | — | — | — | — | — | — | — | C | — | — | — |
| | 5.6050 | — | — | C | — | — | — | 80 | 90 | 0 | 15 | — | 0 | — | — |
| | 1.1210 | 25 | 75 | — | — | — | — | — | — | — | — | 20 | — | — | — |
| | 1.1210 | — | — | 85 | — | — | — | 50 | 20 | 0 | 10 | — | 0 | — | — |
| 38 | 5.6050 | C | C | — | — | — | — | — | — | — | — | C | — | — | — |
| | 5.6050 | — | — | C | — | — | — | C | — | — | C | — | C | C | C |
| | 1.1210 | — | — | C | — | — | — | C | — | — | 70 | — | 99 | 80 | C |
| | 1.1210 | C | C | — | — | — | — | — | — | — | — | C | — | — | — |
| | 0.2803 | C | C | — | — | — | — | — | — | — | — | 99 | — | — | — |
| | 0.2803 | — | — | C | — | — | — | C | — | — | 25 | — | 90 | 75 | C |
| | 0.0701 | 98 | C | — | — | — | — | — | — | — | — | 99 | — | — | — |
| | 0.0701 | — | — | C | — | — | — | C | — | — | 15 | — | 95 | 65 | C |
| | 0.0175 | 70 | 99 | — | — | — | — | — | — | — | — | 65 | — | — | — |
| | 0.0175 | — | — | 90 | — | — | — | 75 | — | — | 0 | — | 75 | 20 | 75 |
| | 0.0044 | 0 | 25 | — | — | — | — | — | — | — | — | 40 | — | — | — |
| | 0.0044 | — | — | 15 | — | — | — | 35 | — | — | 0 | — | 0 | 0 | 0 |
| 39 | 5.6050 | C | C | C | — | — | — | — | — | — | — | — | — | — | — |
| | 1.1210 | C | C | C | — | — | — | — | — | — | — | — | — | — | — |
| | 0.2803 | 99 | C | 95 | — | — | — | — | — | — | — | — | — | — | — |
| | 0.0701 | 45 | 90 | 85 | — | — | — | — | — | — | — | — | — | — | — |
| | 0.0175 | 0 | 90 | 0 | — | — | — | — | — | — | — | — | — | — | — |
| | 0.0087 | 0 | 45 | 0 | — | — | — | — | — | — | — | — | — | — | — |

Post-Emergent Herbicide Activity on Plants

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table C. The post-emergent herbicidal activity index used in Table C is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — or a blank |
| Species planted, no data | N |

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/ha. The pans were returned to the greenhouse and watered as before and the injury to the plants as compared to those in control pans was observed at approximately 10–14 days (usually 11 days). the plant identifying codes in Table C are the same as above defined.

TABLE C

Herbicide Primary Post, spectrums 25 and 90
(C = 100% control)

| Ex. No. | Rate CP kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 30 | 0 | 60 | 0 | 70 | 60 | 40 | 50 | 70 | 60 | — | — | — | — | — |
| 2 | 11.2100 | 0 | 0 | 10 | 0 | 0 | 20 | 20 | 10 | 10 | 10 | — | — | — | — | — |
| 3 | 11.2100 | 0 | 0 | 0 | 0 | 0 | 10 | 0 | 0 | 20 | 10 | — | — | — | — | — |
| 4 | 11.2100 | 0 | 0 | 0 | 10 | 0 | 30 | 30 | 40 | 40 | 40 | — | — | — | — | — |
| 5 | 11.2100 | 0 | 0 | 20 | 0 | 0 | 30 | 30 | 30 | 20 | 30 | — | — | — | — | — |
| 6 | 11.2100 | 0 | 0 | 0 | 0 | 0 | 20 | 40 | 30 | 40 | 10 | — | — | — | — | — |
| 7 | 11.2100 | 0 | 0 | 50 | 10 | 30 | 50 | 40 | 50 | 50 | 60 | — | — | — | — | — |
| 8 | 11.2100 | 0 | 0 | 0 | 0 | 0 | 30 | 30 | 20 | 10 | 20 | — | — | — | — | — |
| 9 | 11.2100 | 0 | 0 | 10 | 0 | 0 | 20 | 20 | 20 | 20 | 10 | — | — | — | — | — |
| 10 | 11.2100 | 0 | 0 | 40 | 0 | 20 | 20 | 30 | 10 | 20 | 30 | — | — | — | — | — |
| 11 | 11.2100 | 0 | 20 | 50 | 0 | 20 | 0 | 50 | 0 | 10 | 30 | — | — | — | — | — |
| 12 | 11.2100 | 0 | 0 | 0 | 0 | 0 | 20 | 20 | 10 | 10 | 10 | — | — | — | — | — |
| 13 | 11.2100 | 0 | 0 | 0 | 0 | 0 | 10 | 10 | 0 | 10 | 0 | — | — | — | — | — |
| 14 | 11.2100 | 0 | 0 | 0 | 0 | 0 | 0 | 20 | 10 | 20 | 10 | — | — | — | — | — |
| 15 | 11.2100 | 0 | 0 | 0 | 0 | 0 | 0 | 10 | 0 | 10 | 10 | — | — | — | — | — |
| 16 | 11.2100 | 0 | 0 | 0 | 0 | 20 | 40 | 10 | 50 | 30 | N | — | — | — | — | — |
| 17 | 11.2100 | 0 | 0 | 70 | 0 | 50 | 40 | 30 | 30 | 40 | 50 | — | — | — | — | — |
| 18 | 11.2100 | 0 | 0 | 0 | 0 | 0 | 0 | 0 | 0 | 0 | 0 | — | — | — | — | — |
| 19 | 11.2100 | 30 | 0 | 30 | 0 | 20 | 20 | 20 | 10 | 0 | 20 | — | — | — | — | — |
| 20 | 11.2100 | 0 | 10 | 0 | 0 | 0 | 20 | 40 | 20 | 20 | 20 | — | — | — | — | — |
| 21 | 11.2100 | 0 | 10 | 30 | 0 | 30 | 0 | 20 | 0 | 20 | 20 | — | — | — | — | — |
| 22 | 11.2100 | 0 | 10 | 0 | 0 | 0 | 10 | 0 | 0 | 20 | 10 | — | — | — | — | — |
| 23 | 11.2100 | 0 | 0 | 40 | 0 | 50 | 40 | 30 | 40 | 60 | 60 | — | — | — | — | — |
| 24 | 11.2100 | 0 | 20 | 20 | 10 | 40 | 40 | 50 | 30 | 50 | 50 | — | — | — | — | — |
| 25 | 11.2100 | 0 | 0 | 50 | 0 | 0 | 50 | 30 | 30 | 50 | 50 | — | — | — | — | — |
| 26 | 11.2100 | 0 | 0 | 80 | 20 | 80 | 50 | 50 | 40 | 40 | 60 | — | — | — | — | — |
| 27 | 11.2100 | 0 | 0 | 30 | 0 | 30 | 60 | 30 | 50 | 50 | 50 | — | — | — | — | — |
| 28 | 11.2100 | 0 | 0 | 0 | 0 | 0 | 0 | 0 | 0 | 0 | 0 | — | — | — | — | — |
| 29 | 11.2100 | 0 | 0 | 50 | 20 | 20 | 50 | 30 | 40 | 50 | 50 | — | — | — | — | — |
| 30 | 11.2100 | 0 | 0 | 0 | 0 | 0 | 0 | 0 | 0 | 0 | 0 | — | — | — | — | — |
| 31 | 11.2100 | 0 | 0 | 50 | 0 | 0 | 40 | 50 | 40 | 50 | 60 | — | — | — | — | — |
| 32 | 11.2100 | 0 | 0 | 50 | 20 | 30 | 60 | 50 | 50 | 60 | 50 | — | — | — | — | — |
| 33 | 11.2100 | 0 | 0 | 50 | 0 | 60 | 50 | 50 | 50 | 60 | 60 | — | — | — | — | — |
| 34 | 11.2100 | 0 | 20 | 60 | 10 | 10 | 30 | 40 | 40 | 50 | 30 | — | — | — | — | — |
| 35 | 11.2100 | 0 | 0 | 0 | 0 | 0 | 20 | 20 | 0 | 0 | 10 | — | — | — | — | — |
| 36 | 11.2100 | 0 | 0 | 0 | 0 | 0 | 10 | 0 | 10 | 0 | 10 | — | — | — | — | — |
| 37 | 11.2100 | 0 | 0 | 0 | 0 | 0 | 10 | 30 | 10 | 10 | 10 | — | — | — | — | — |
| 38 | 11.2100 | 0 | 0 | 0 | 0 | 0 | 30 | 30 | 30 | 30 | 30 | — | — | — | — | — |
| 39 | 11.2100 | 0 | 0 | 10 | 0 | 10 | 30 | 20 | 20 | 10 | 40 | — | — | — | — | — |

Compounds of this invention were also tested for herbicidal activity on weed plants in the presence of crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mol of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10-14 days (usually 11 days).

In the following Table D the legends used to identify the plant species are the same as those used in the preceding Table B.

TABLE D

Herbicide Secondary Post,
spectrums 26, 88, 91, 93, 95, 96, and 100
(C = 100% control)

| Ex. No. | Rate kg/ha | Sobe | Cotz | Rape | Cobu | Wibw | Mogl | Hese | Jiwe | Vele | Whez | Rice | Grso | Corn | Dobr | Prmi |
|---|---|---|---|---|---|---|---|---|---|---|---|---|---|---|---|---|
| 1 | 5.6050 | 75 | 75 | 90 | 85 | 75 | 75 | 95 | 85 | 80 | 30 | 20 | 75 | 95 | 20 | 65 |
|   | 1.1210 | 75 | 60 | 85 | 75 | 60 | 70 | 95 | 85 | 85 | 0 | 20 | 50 | 95 | 0 | 0 |

TABLE D-continued

Herbicide Secondary Post,
spectrums 26, 88, 91, 93, 95, 96, and 100
(C = 100% control)

|    |         |    |    |    |    |    |    |    |    |    |    |    |    |    |    |    |
|----|---------|----|----|----|----|----|----|----|----|----|----|----|----|----|----|----|
|    | 0.2803  | 50 | 60 | 80 | 50 | 0  | 50 | 90 | 75 | 80 | 0  | 0  | 20 | 80 | 0  | 0  |
|    | 0.0701  | 70 | 40 | 80 | 20 | 0  | 50 | 80 | 75 | 30 | 0  | 0  | 0  | 70 | 0  | 0  |
| 2  | 5.6050  | 60 | 40 | 80 | 75 | 40 | 50 | 50 | —  | 60 | 5  | 5  | 30 | 50 | 5  | 0  |
|    | 1.1210  | 65 | 35 | 80 | 70 | 40 | 60 | 65 | —  | 70 | 0  | 5  | 5  | 60 | 0  | 0  |
|    | 0.2803  | 65 | 10 | 80 | 60 | 20 | 50 | 65 | —  | 60 | 0  | 0  | 60 | 60 | 0  | 0  |
|    | 0.0701  | 25 | 20 | 80 | 50 | 0  | 25 | 40 | —  | 50 | 0  | 10 | 5  | 10 | 0  | 0  |
| 26 | 11.2100 | —  | —  | 80 | —  | 80 | —  | —  | —  | —  | 10 | —  | —  | —  | 10 | —  |
|    | 11.2100 | 75 | 75 | —  | 80 | —  | 80 | —  | —  | 75 | —  | 10 | —  | 80 | —  | —  |
|    | 5.6050  | 50 | 75 | —  | 75 | —  | 80 | —  | —  | 80 | —  | 30 | —  | 60 | —  | —  |
|    | 5.6050  | —  | —  | 80 | —  | 75 | —  | —  | —  | —  | 5  | —  | —  | —  | 0  | —  |
|    | 1.1210  | —  | —  | 80 | —  | 65 | —  | —  | —  | —  | 0  | —  | —  | —  | 0  | —  |
|    | 1.1210  | 60 | 60 | —  | 75 | —  | 75 | —  | —  | 80 | —  | 10 | —  | 65 | —  | —  |
|    | 0.2803  | 25 | 60 | —  | 75 | —  | 75 | —  | —  | 80 | —  | 0  | —  | 60 | —  | —  |
|    | 0.2803  | —  | —  | 80 | —  | 60 | —  | —  | —  | —  | 0  | —  | —  | —  | 0  | —  |
| 32 | 5.6050  | 50 | 50 | —  | 70 | —  | 75 | —  | —  | 70 | —  | 0  | —  | 50 | —  | —  |
|    | 5.6050  | —  | —  | 50 | —  | 50 | —  | —  | —  | —  | 20 | —  | —  | —  | 0  | —  |
|    | 1.1210  | 25 | 50 | —  | 70 | —  | 70 | —  | —  | 75 | —  | 0  | —  | 10 | —  | —  |
|    | 1.1210  | —  | —  | 60 | —  | 50 | —  | —  | —  | —  | 0  | —  | —  | —  | 0  | —  |
|    | 0.2803  | 5  | 40 | —  | 40 | —  | 30 | —  | —  | 30 | —  | N  | —  | 0  | —  | —  |
|    | 0.2803  | —  | —  | 30 | —  | 35 | —  | —  | —  | —  | 0  | —  | —  | —  | 0  | —  |
| 33 | 5.6050  | 65 | 70 | —  | 75 | —  | 75 | —  | —  | 80 | —  | 0  | —  | 40 | —  | —  |
|    | 5.6050  | —  | —  | 50 | —  | 70 | —  | —  | —  | —  | 10 | —  | —  | —  | 0  | —  |
|    | 1.1210  | 60 | 60 | —  | 75 | —  | 75 | —  | —  | 80 | —  | 0  | —  | 25 | —  | —  |
|    | 1.1210  | —  | —  | 35 | —  | 60 | —  | —  | —  | —  | 0  | —  | —  | —  | 0  | —  |
|    | 0.2803  | 5  | 50 | —  | 70 | —  | 50 | —  | —  | 70 | —  | 0  | —  | 25 | —  | —  |
|    | 0.2803  | —  | —  | 35 | —  | 40 | —  | —  | —  | —  | 0  | —  | —  | —  | 0  | —  |

| Ex. No. | Rate kg/ha | Bygr | Lacg | Grft | Sube | Colq | Pesw | Cocw | Anbg | Barz | Ruth | Sejg | Wioa | Cwbs | Blgr |
|---------|-----------|------|------|------|------|------|------|------|------|------|------|------|------|------|------|
| 1  | 5.6050  | 70 | 95 | 50 | — | — | — | —  | —  | —  | —  | —  | —  | —  | —  |
|    | 1.1210  | 60 | 95 | 50 | — | — | — | —  | —  | —  | —  | —  | —  | —  | —  |
|    | 0.2803  | 0  | 75 | 0  | — | — | — | —  | —  | —  | —  | —  | —  | —  | —  |
|    | 0.0701  | 0  | 75 | 0  | — | — | — | —  | —  | —  | —  | —  | —  | —  | —  |
| 2  | 5.6050  | 25 | 60 | 25 | — | — | — | 80 | —  | —  | —  | —  | —  | —  | —  |
|    | 1.1210  | 0  | 65 | 0  | — | — | — | 70 | —  | —  | —  | —  | —  | —  | —  |
|    | 0.2803  | 10 | 50 | 5  | — | — | — | 50 | —  | —  | —  | —  | —  | —  | —  |
|    | 0.0701  | 0  | 30 | 0  | — | — | — | 40 | —  | —  | —  | —  | —  | —  | —  |
| 26 | 11.2100 | —  | —  | 80 | — | — | — | 90 | 25 | 10 | N  | —  | 10 | —  | —  |
|    | 11.2100 | 50 | 95 | —  | — | — | — | —  | —  | —  | —  | 0  | —  | —  | —  |
|    | 5.6050  | 20 | 90 | —  | — | — | — | —  | —  | —  | —  | 0  | —  | —  | —  |
|    | 5.6050  | —  | —  | 75 | — | — | — | 80 | 0  | 5  | N  | —  | 10 | —  | —  |
|    | 1.1210  | —  | —  | 50 | — | — | — | 75 | 0  | 5  | N  | —  | 10 | —  | —  |
|    | 1.1210  | 10 | 95 | —  | — | — | — | —  | —  | —  | —  | N  | —  | —  | —  |
|    | 0.2803  | 0  | 80 | —  | — | — | — | —  | —  | —  | —  | 0  | —  | —  | —  |
|    | 0.2803  | —  | —  | 25 | — | — | — | 75 | 0  | 0  | N  | —  | 0  | —  | —  |
| 32 | 5.6050  | 0  | 50 | —  | — | — | — | —  | —  | —  | —  | 0  | —  | —  | —  |
|    | 5.6050  | —  | —  | 20 | — | — | — | 60 | 15 | 20 | 10 | —  | 30 | —  | —  |
|    | 1.1210  | 0  | 60 | —  | — | — | — | —  | —  | —  | —  | 0  | —  | —  | —  |
|    | 1.1210  | —  | —  | 10 | — | — | — | 20 | 0  | 0  | 0  | —  | 0  | —  | —  |
|    | 0.2803  | 0  | 0  | —  | — | — | — | —  | —  | —  | —  | 0  | —  | —  | —  |
|    | 0.2803  | —  | —  | 0  | — | — | — | 10 | 0  | 0  | 0  | —  | 0  | —  | —  |
| 33 | 5.6050  | 30 | 90 | —  | — | — | — | —  | —  | —  | —  | 20 | —  | —  | —  |
|    | 5.6050  | —  | —  | 30 | — | — | — | 80 | 20 | 10 | 20 | —  | 10 | —  | —  |
|    | 1.1210  | 0  | 90 | —  | — | — | — | —  | —  | —  | —  | 0  | —  | —  | —  |
|    | 1.1210  | —  | —  | 15 | — | — | — | 55 | 0  | 0  | 20 | —  | 0  | —  | —  |
|    | 0.2803  | 0  | 75 | —  | — | — | — | —  | —  | —  | —  | 0  | —  | —  | —  |
|    | 0.2803  | —  | —  | 0  | — | — | — | 55 | 0  | 0  | 0  | —  | 0  | —  | —  |

As can be seen from the data above, some of the compounds appear to be quite safe on certain crops and may be useful for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting an d dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,-N-dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. these extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ehtylamino)-s-triazine
3-Isopropyl-1H-2,1,3-benzothiadiazine-4-(3H)-one, 2,2 dioxide
3-Amino-1,2,4-triazole
6,7-Dihydrodipyrido(1,2-d:α',1'-c)-pyrazidinium salt
5-Bromo-3-isopropyl-6-methyluracil 1,1'-dimethyl-4,4'-bipyridinium
2-(4-isopropyl-4-methyl-5-oxo-2-imidazolin-2-yl)- 3-quinolinecarboxylic acid
Isopropylamine salt of 2-(4-isopropyl-4-methyl-5- oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-Dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl) aminocarbonyl)amino sulfonyl methyl) benzoate
Methyl 2-(((((4-methoxy-6-methyl-1,3,5-triazin-2-yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate Acetamides/Actanilides/Anilines/Amides 2-Chloro-N,N-diallylacetamide
N,N-dimethyl-2,2-diphenylacetamide
N-(2,4-dimethyl-5-[[(trifluoromethyl)sulfonyl] amino] phenyl]acetamide N-Isopropyl-2-chloroacetanilide
2',6'-Diethyl-N-methoxymethyl-2-chloroacetanilide 2′-Methyl-6′-ethyl-N-(2-methoxypropyl-2yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]proprionate
3-Amino-2,5-dichlorobenzoic acid
2-Methoxy-3,6-dichlorobenzoic acid
2,3,6-Trichloropehnylacetic acid
N-1-naphthylphthalamic acid
Sodium-5-[2-chloro-4-(trifluoromethyl)phenoxy]-2-nitrobenzoate
4,6-Dinitro-o-(sec-butyl)phenol N-(phosphonomethyl) glycine and its salts.
Butyl 2-[4-[(5-trifluoromethyl)-2-pyridinyl)oxy]phenoxy]-propanoate Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methyl sulfonyl 2-nitrobenzamide
1′-(Carboethoxy) ethyl 5-[2-chloro-4-(trifluoro methyl)-phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below. When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5,60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus, the term refers to any substance or medium in which vegetation may take root and grow, and includes not only earth but also compost, manure, muck, humus, sand, and the like, adapted to support plant growth.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skills in the art to which the invention pertains.

What is claimed is:

1. A compound represented by the formula

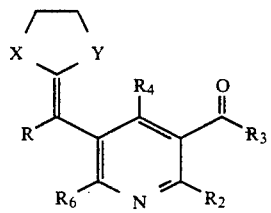

wherein
R is hydrogen, cyano, halo, or lower alkoxycarbonyl;
$R_2$ and $R_6$ are independently lower alkyl, chloromethyl, fluoromethyl, chlorofluoromethyl, lower alkoxy, or lower dialkoxyalkyl, provided that one of $R_2$ and $R_6$ must be a fluoromethyl or chloromethyl;
$R_3$ is hydroxy, lower alkoxy, lower alkylthio, $C_1$-$C_7$ haloalkoxy, lower alkenyloxy, lower alkynyloxy, $C_1$-$C_{14}$ (di)alkylamino, or phenylamino;
$R_4$ is $C_1$-$C_4$ straight or branched chain alkyl, $C_3$-$C_4$ cycloalkyl, $C_4$-$C_8$ cycloalkylalkyl, $C_1$-$C_7$ haloalkyl, lower alkoxyalkyl, lower alkylthioalkyl, or $C_2$-$C_{14}$ dialkylaminoalkyl;
X and Y are independently O, S, $CH_2$, CHR′, CR′R″, or NHR‴;
R′ and R″ are independently lower alkyl, halo, cyano, hydroxy, lower alkoxy, or lower alkylthio; and
R‴ is hydrogen or lower alkyl.

2. The compound of claim 1 wherein one of $R_2$ and $R_6$ is difluoromethyl and the other is trifluoromethyl.

3. The compound of claim 2 wherein $R_3$ is lower alkoxy or lower alkylthio.

4. The compound of claim 3 wherein $R_4$ is $C_1$-$C_4$ straight or branched chain alkyl, $C_3$-$C_4$ cycloalkyl, or $C_4$-$C_8$ cycloalkylalkyl.

5. The compound of claim 4 wherein R is cyano.

6. The compound of claim 5 wherein Y is $CH_2$.

7. The compound of claim 6 wherein X is O.

8. A method of controlling undesirable vegetation comprising applying thereto an effective amount of a compound of the formula $$\begin{array}{c} X \overset{\frown}{\phantom{x}} Y \\ R \end{array} \begin{array}{c} R_4 \quad O \\ \| \\ R_3 \end{array}$$
$$R_6 \quad N \quad R_2$$

wherein R is hydrogen, cyano, halo, or lower alkoxycarbonyl;

- $R_2$ and $R_6$ are independently lower alkyl, chloromethyl, fluoromethyl, chlorofluoromethyl, lower alkoxy, or lower dialkoxyalkyl, provided that one of $R_2$ and $R_6$ must be a fluoromethyl or chloromethyl;
- $R_3$ is hydrogen, lower alkoxy, lower alkylthio, $C_1$–$C_7$ haloalkoxy, lower alkenyloxy, lower alkynyloxy, $C_1$–$C_{14}$ (di)alkylamino, or phenylamino;
- $R_4$ is $C_1$–$C_4$ straight or branched chain alkyl, $C_3$–$C_4$ cycloalkyl, $C_4$–$C_8$ cycloalkylalkyl, $C_1$–$C_7$ haloalkyl, lower alkoxyalkyl, lower alkylthioalkyl, or $C_2$–$C_{14}$ dialkylaminoalkyl;
- X and Y are independently O, S, $CH_2$, CHR', CR'R'', or NHR''';
- R' and R'' are independently lower alkyl, halo, cyano, hydroxy, lower alkoxy, or lower alkylthio; and
- R''' is hydrogen or lower alkyl.

9. The method of claim 8 wherein one of $R_2$ and $R_6$ is difluoromethyl and the other is trifluoromethyl.

10. The method of claim 9 wherein $R_3$ is alkoxy or lower alkylthio.

11. The method of claim 10 wherein $R_4$ is $C_1$–$C_4$ straight or branched chain alkyl, $C_3$–$C_4$ cycloalkyl, or $C_4$–$C_8$ cycloalkylalkyl.

12. The method of claim 11 wherein R is cyano.

13. The method of claim 12 wherein Y is $CH_2$.

14. The method of claim 13 wherein X is O.

15. A herbicidal composition comprising an inert ingredient and an effective amount of an active ingredient of the formula $$\begin{array}{c} X \overset{\frown}{\phantom{x}} Y \\ R \end{array} \begin{array}{c} R_4 \quad O \\ \| \\ R_3 \end{array}$$
$$R_6 \quad N \quad R_2$$

wherein R is hydrogen, cyano, halo, or lower alkoxycarbonyl;

- $R_2$ and $R_6$ are independently lower alkyl, chloromethyl, fluoromethyl, chlorofluoromethyl, lower alkoxy, or lower dialkoxyalkyl, provided that one of $R_2$ and $R_6$ must be a fluoromethyl or chloromethyl;
- $R_3$ is hydroxy, lower alkoxy, lower alkylthio, $C_1$–$C_7$ haloalkoxy, lower alkenyloxy, lower alkynyloxy, $C_1$–$C_{14}$ (di)alkylamino, or phenylamino;
- $R_4$ is $C_1$–$C_4$ straight or branched chain alkyl, $C_3$–$C_4$ cycloalkyl, $C_4$–$C_8$ cycloalkyalkyl, $C_1$–$C_7$ haloalkyl, lower alkoxyalkyl, lower alkylthioalkyl, or $C_2$–$C_{14}$ dialkylaminoalkyl;
- X and Y are independently O, S, $CH_2$, CHR', CR'R'', or NHR''';
- R' and R'' are independently lower alkyl, halo, cyano, hydroxy, lower alkoxy, or lower alkylthio; and
- R''' is hydrogen or lower alkyl.

16. The composition of claim 15 wherein one of $R_2$ and $R_6$ is difluormethyl and the other is trifluoromethyl.

17. The composition of claim 16 wherein $R_3$ is lower alkoxy or lower alkylthio.

18. The composition of claim 17 wherein $R_4$ is $C_1$–$C_4$ straight or branched chain alkyl, $C_3$–$C_4$ cycloalkyl, or $C_4$–$C_8$ cycloalkylalkyl.

19. The composition of claim 18 wherein R is cyano.

20. The composition of claim 19 wherein Y is $CH_2$.

21. The composition of claim 20 wherein X is O.

* * * * *